(12) United States Patent
Burbank et al.

(10) Patent No.: US 8,066,524 B2
(45) Date of Patent: Nov. 29, 2011

(54) SURGICAL SYSTEM WITH ELECTRO-MECHANICAL INTERFACES TO MOUNT ROBOTIC SURGICAL ARMS

(75) Inventors: William A. Burbank, Sandy Hook, CT (US); Scott Luke, Ben Lomond, CA (US); Dean F. Hoorneart, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 12/793,871

(22) Filed: Jun. 4, 2010

(65) Prior Publication Data
US 2010/0241138 A1    Sep. 23, 2010

Related U.S. Application Data

(62) Division of application No. 11/466,097, filed on Aug. 21, 2006, now Pat. No. 7,762,825.

(60) Provisional application No. 60/752,446, filed on Dec. 20, 2005.

(51) Int. Cl.
*H01R 13/64* (2006.01)
(52) U.S. Cl. ......................................... 439/247; 439/248
(58) Field of Classification Search .................. 439/247, 439/248
See application file for complete search history.

(56) References Cited

U.S. PATENT DOCUMENTS

| | | | |
|---|---|---|---|
| 3,673,545 A | 6/1972 | Rundle | |
| 4,664,588 A | 5/1987 | Newell et al. | |
| 4,812,133 A | 3/1989 | Fleak et al. | |
| 4,909,748 A | 3/1990 | Kozono et al. | |
| 5,035,396 A | 7/1991 | Krum et al. | |
| 5,071,374 A | 12/1991 | Plocek et al. | |
| 5,605,150 A | 2/1997 | Radons et al. | |
| 5,752,845 A | 5/1998 | Fu | |
| 5,902,149 A | 5/1999 | Tashiro et al. | |
| 6,033,247 A | 3/2000 | Gregory, II | |
| 6,358,075 B1 | 3/2002 | Tischner | |
| 6,592,387 B2 | 7/2003 | Komenda et al. | |
| 6,736,659 B1 | 5/2004 | Wu | |
| 6,739,891 B2 * | 5/2004 | Itoh .............................. | 439/174 |
| 6,788,018 B1 | 9/2004 | Blumenkranz | |
| 7,014,486 B1 | 3/2006 | Wu et al. | |
| 2007/0142971 A1 | 6/2007 | Schena | |

FOREIGN PATENT DOCUMENTS

DE     19844281 A1     5/2000

(Continued)

OTHER PUBLICATIONS

U.S. Appl. No. 11/466,097 Office Action mailed Oct. 21, 2009, 20 pages.

(Continued)

*Primary Examiner* — Tho D Ta

(57) ABSTRACT

In one embodiment of the invention, a method of mounting a surgical robotic arm to a set-up arm of a robotic surgical system is provided that includes sliding a pair of guide slots of the surgical robotic arm over a pair of guide tabs in the set-up arm; aligning electrical connectors in the set-up arm to electrical connectors of the surgical robotic arm; and coincidentally mating male electrical connectors to female electrical connectors while finally mating the guide tabs in the set-up arm to flanges of a housing of the surgical robotic arm.

9 Claims, 19 Drawing Sheets

FOREIGN PATENT DOCUMENTS

| | | |
|---|---|---|
| FR | 2618265 A1 | 1/1989 |
| WO | WO-9614101 A1 | 5/1996 |
| WO | WO-0022700 A1 | 4/2000 |
| WO | WO-2007120330 A3 | 10/2007 |

OTHER PUBLICATIONS

ATI Industrial Automation, "Automatic / Robotic Tool Changers," 2005, 2 pages. Internet: http://www.ati-ia.com/products/toolchanger/robot_tool_changer.aspx as displayed on the Wayback Machine at www.archive.org for Oct. 16, 2006.

Gottschalk, Mark A., "Dextrous Manipulator Targets Hazardous Environments," Design News Magazine, Feb. 10, 1992, pp. 140-141.

NASA, "NASA's Innovators: Building Smarter, Tougher Telerobots," NASA TechBriefs, Aug. 1991, pp. 11 and 92.

Odetics, "Odetics Dextrous Manipulator Design Brief," 2006, 8 pages. Internet: http://silicontraption.com/odetics_arm.htm.

PCT/US06/62018 Written Opinion of the International Search Authority, mailed Apr. 22, 2008, 10 pages.

Positronic Industries, Data Sheet for "Blind Mating System and Vibration Locking System, Rear Panel Mount," p. 11 of Subminiature-D Accessories Catalog, posted online Dec. 7, 2004, Internet: http://www.connectpositronic.com/downloads/pdf/c007revc1_c007-1revnc_subdaccess.pdf.

Southco, Data Sheets for Southco V7 Draw Latch Over-Center Series, 2003, pp. 80-83 of online catalog; Internet: http://www.southco.com/resources/documents/v7.en.pdf.

Vertut, Jean and Phillipe Coiffet, "Robot Technology: Teleoperation and Robotics Evolution and Development—Volume 3A", English translation Prentice-Hall, Inc., Inglewood Cliffs, NJ, USA 1986, vol. 3A, 332 pages.

\* cited by examiner

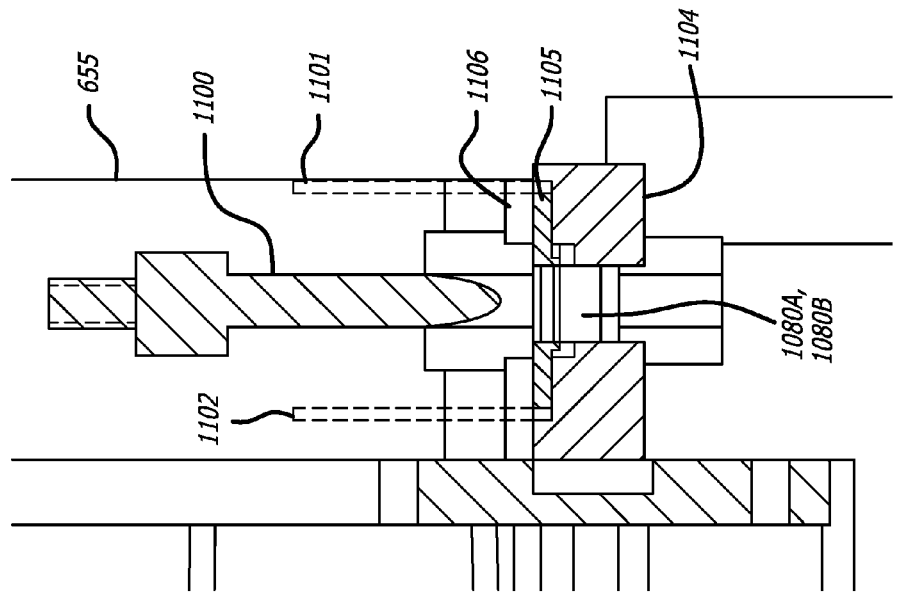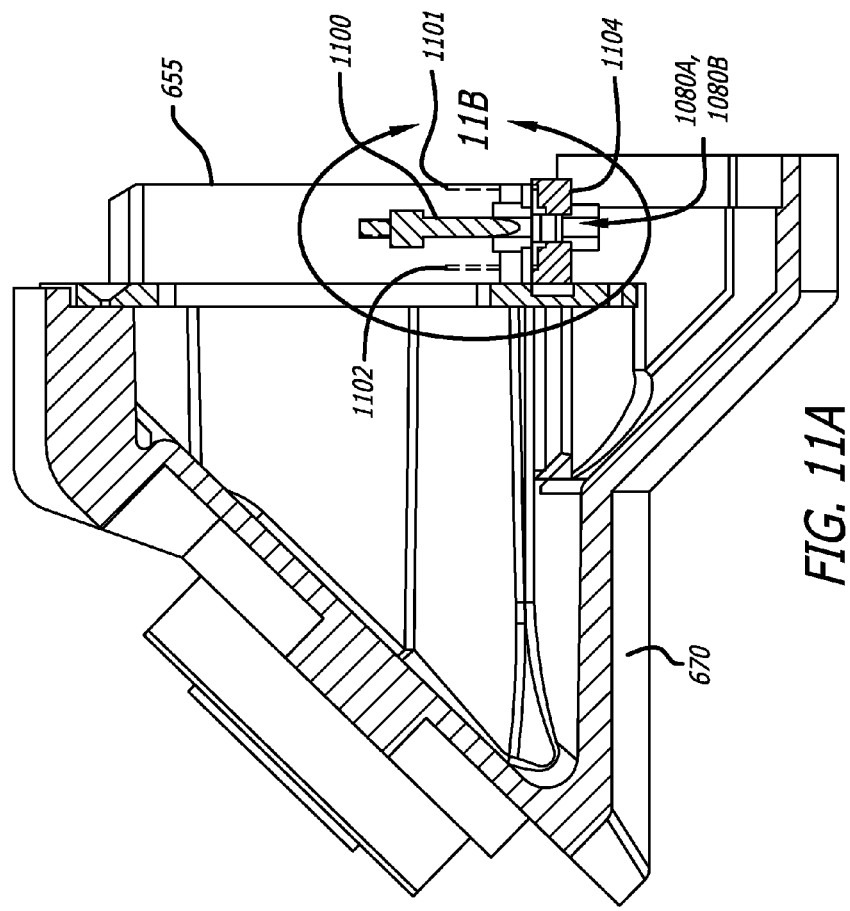

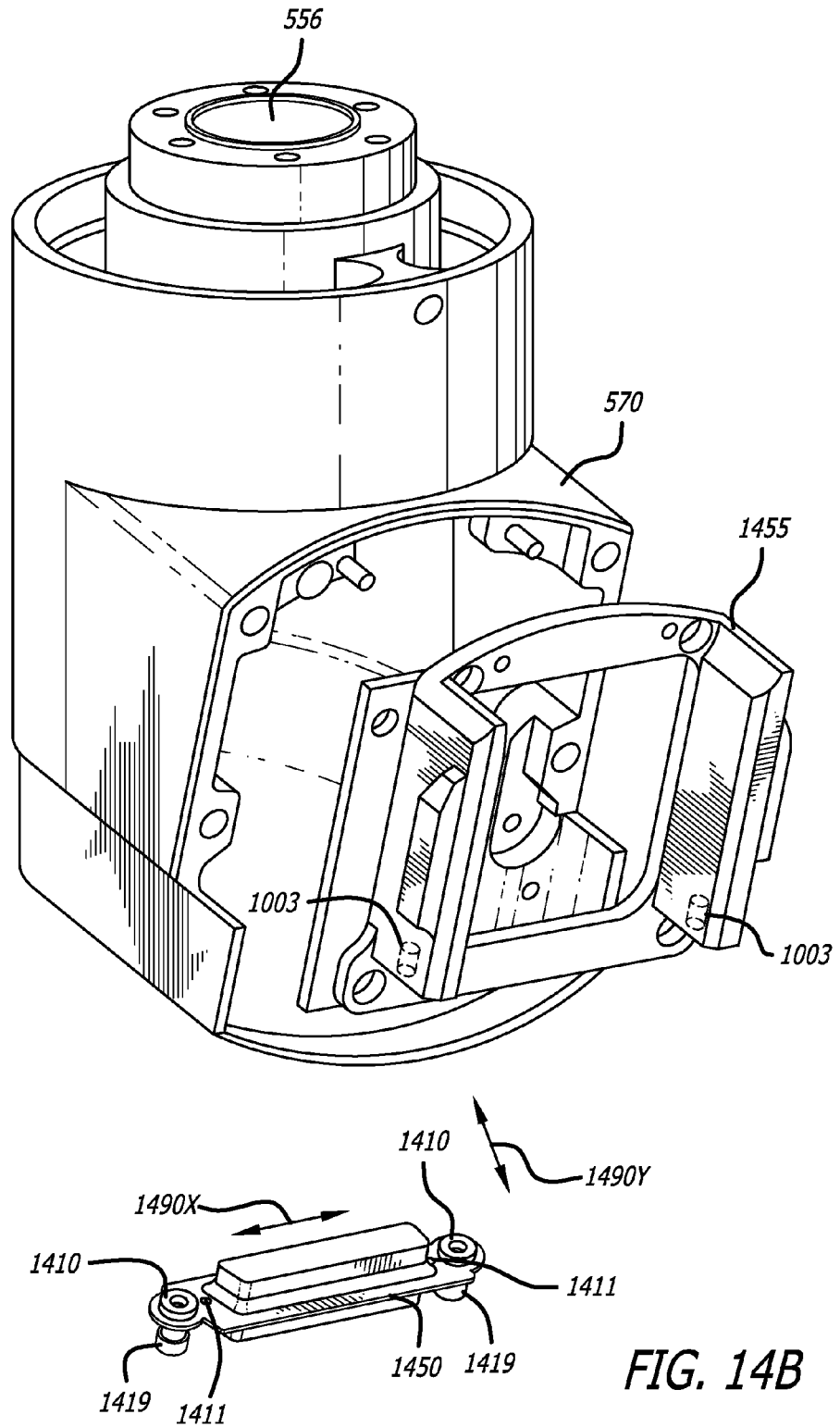

SURGICAL SYSTEM WITH ELECTRO-MECHANICAL INTERFACES TO MOUNT ROBOTIC SURGICAL ARMS

CROSS REFERENCE TO RELATED APPLICATIONS

This non-provisional patent application claims the benefit of and is a divisional of U.S. patent application Ser. No. 11/466,097, entitled ELECTRO-MECHANICAL INTERFACES TO MOUNT ROBOTIC ARMS, filed by William Burbank et al. on Aug. 21, 2006, now issued as U.S. Pat. No. 7,762,825, which claims the benefit of U.S. Provisional Patent Application No. 60/752,446 entitled, "Slidable Electro-Mechanical Interfaces for Mounting Robotic Surgical Arms, filed by William Burbank et al. on Dec. 20, 2005."

FIELD

The embodiments of the invention relate generally to robotic surgical systems. More particularly, the embodiments of the invention relate to mounting and dismounting robotic surgical arms to robotic surgical systems and the electro-mechanical interfaces to do so.

BACKGROUND

Robotic surgery systems are used to perform minimally invasive robotic surgical procedures. Should one of the robotic surgical arms fail for some reason, it is desirable to replace it as quickly as possible to continue the surgery and/or perform additional procedures. If one of a plurality of robotic surgical arms of the system is not being used, it may be used to swap out the failing arm. Alternatively, a spare robotic surgical arm may be used to swap out a defective or failing robotic surgical arm. In some other cases, a robotic surgical arm may be swapped out for maintenance, adjustments, and/or cleaning. As a typical robotic surgical arm is relatively heavy, swapping out a robotic surgical arm is difficult and time consuming for one person. Thus, there is room for improvement in robotic surgical systems to ease the swapping of robotic surgical arms into and out of a robotic surgical system.

BRIEF SUMMARY

The embodiments of the invention are summarized by the claims that follow below.

BRIEF DESCRIPTIONS OF THE DRAWINGS

FIG. 1 is a block diagram of a robotic surgery system to perform minimally invasive robotic surgical procedures using one or more robotic surgical arms with a strap drive train.

FIG. 2 a perspective view of the robotic patient-side system of FIG. 1 with the one or more robotic surgical arms having the strap drive train.

FIG. 11A is a side cross-sectional view of the exemplary connector portion of the set-up joint portion of FIGS. 6-10.

FIG. 11B is a magnified side cross-sectional view of the exemplary connector portion illustrated in FIG. 11A.

FIG. 14B is an exploded perspective view of a yet another exemplary embodiment of the invention.

It will be appreciated that all the drawings of Figures provided for herein are for illustrative purposes only and do not necessarily reflect the actual shape, size, or dimensions of the elements being illustrated.

DETAILED DESCRIPTION

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention include methods, apparatus and systems for a robotic surgical system. In one embodiment of the invention a robotic surgical system is provided including one or more robotic surgical arms with electro-mechanical interfaces to mount and dismount with electro-mechanical interfaces of set up arms of a patient side system.

Robotic Surgical System

Figure 1:
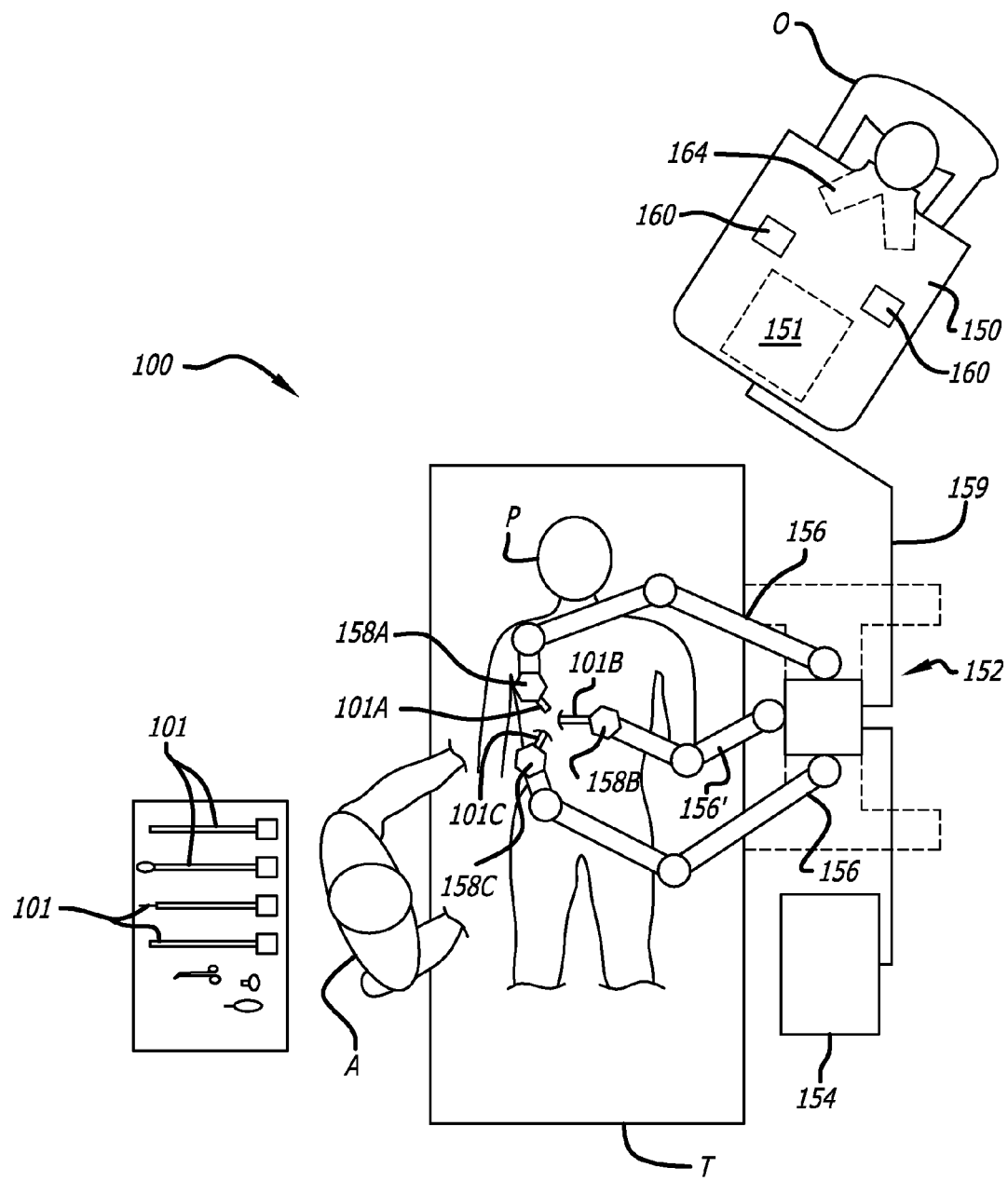

Referring now to FIG. 1, a block diagram of a robotic surgery system 100 is illustrated to perform minimally invasive robotic surgical procedures using one or more robotic arms with strap drive. Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). At least one of the robotic manipulator arms (e.g., the center robotic manipulator arm 158B) is used to support a stereo or three dimensional surgical image capture device 110 such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

A user or operator O (generally a surgeon) performs a minimally invasive surgical procedure on patient P by manipulating control input devices 160 at a master control console 150. A computer 151 of the console 150 directs movement of robotically controlled endoscopic surgical instruments 101A-101C by means of one or more control cables 159, effecting movement of the instruments using a robotic patient-side system 152 (also referred to as a patient-side cart). The robotic patient-side system 152 has one or more robotic arms 158. In a preferred embodiment of the invention, the one or more robotic arms 158 have a strap drive system. Typically, the robotic patient-side system 152 includes at least three robotic manipulator arms 158A-158C supported by linkages 156, 156', with a central robotic arm 158B supporting an endoscopic camera 101B and the robotic arms 158A, 158C to left and right of center supporting tissue manipulation tools 101A and 101C.

Generally, the robotic patient-side system 152 includes a positioning portion and a driven portion. The positioning portion of the robotic patient-side system 152 remains in a fixed configuration during surgery while manipulating tissue. The driven portion of the robotic patient-side system 152 is actively articulated under the direction of the operator O generating control signals at the surgeon's console 150 during surgery. The actively driven portion of the robotic patient-side system 152 is generally referred to herein as the robotic arms or alternatively to robotic surgical manipulators. The positioning portion of the robotic patient-side system 152 that is in a fixed configuration during surgery may be referred to as "set up arms" 156, 156' with positioning linkage and/or "set-up joints" (SUJ). In an alternate embodiment of the invention, the robotic patient-side system 152 may be replaced by set up arms that couple at one end to left and right sides of the operating table T. The three robotic manipulator arms 158A-158C may then be coupled to the opposite end of the set-up arms to ground to the table T.

For convenience in terminology, manipulators such as robotic surgical arms 158A and 158C actuating the tissue affecting surgical tools 101A and 101C are generally referred to herein as a PSM (patient-side manipulators), and a robotic surgical arm 158B controlling an image capture or data acquisition device, such as the endoscopic camera 101B, is generally referred to herein as a ECM (endoscope-camera manipulator), it being noted that such telesurgical robotic manipulators may optionally actuate, maneuver and control a wide variety of instruments, tools and devices useful in surgery. The surgical tools 101A, 101C and endoscopic camera 101B may be generally referred to herein as tools or instruments 101.

An assistant A may assist in pre-positioning of the robotic patient-side system 152 relative to patient P as well as swapping tools or instruments 101 for alternative tool structures, and the like, while viewing the internal surgical site via an assistant's display 154. With the embodiments of the invention, the assistant A may also swap in and out the robotic surgical arms 158A and 158C, as well as the robotic surgical arm 158B, in case one is defective or failing. In other cases, a robotic surgical arm may be swapped out for maintenance, adjustments, or cleaning and then swapped back in by one or more service persons.

Figure 2:
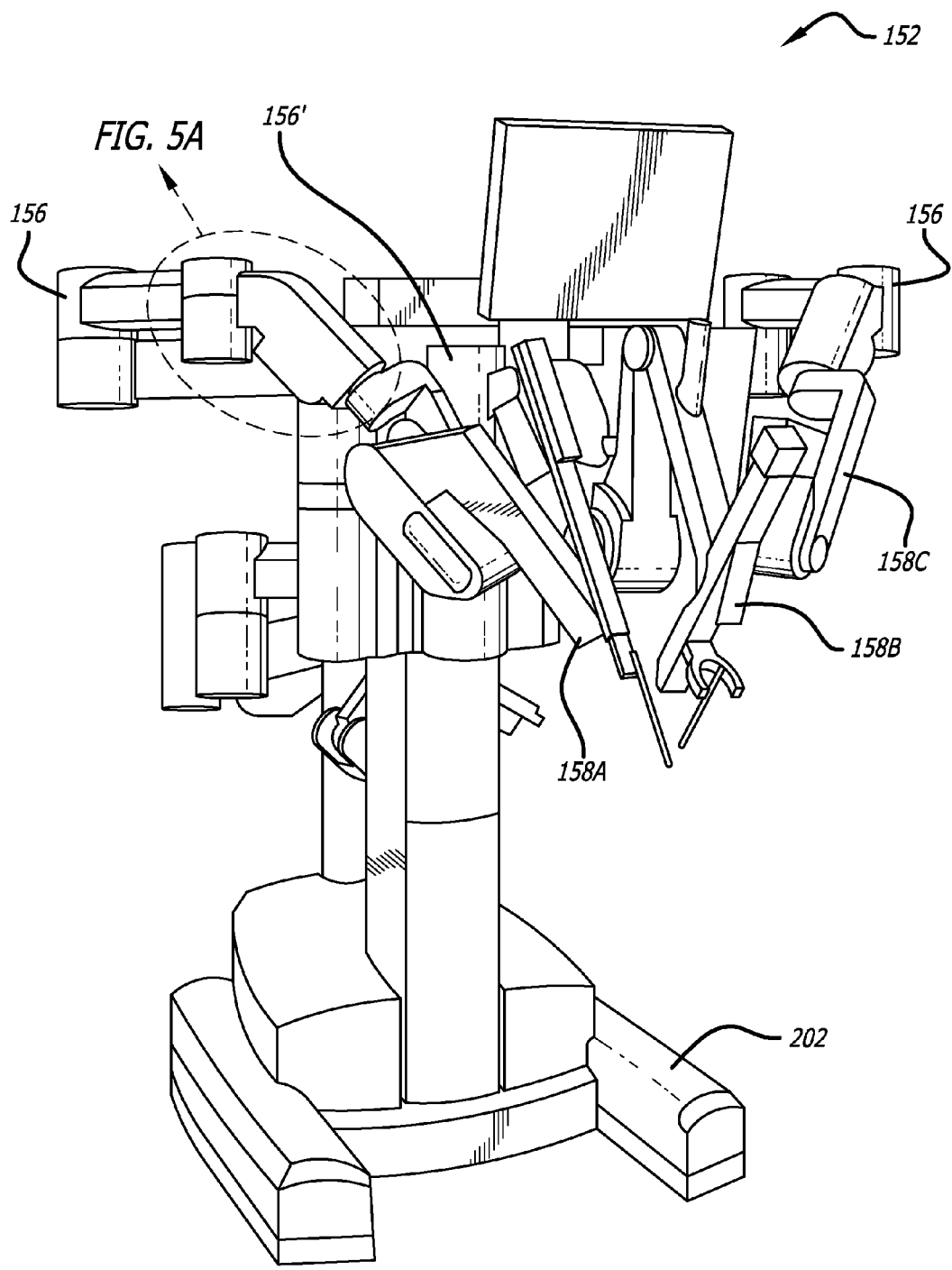

Referring now to FIG. 2, a perspective view of the robotic patient-side system 152 is illustrated. The robotic patient-side system 152 may have one or more robotic surgical arms (a.k.a., robotic surgical manipulators) 158A-158C with a strap drive system. The robotic arms 158A, 158C are for coupling to robotic surgical tools 101A, 101C. The robotic arm 158B is for coupling to an endoscopic camera 101B. Generally, the surgical robotic arms 158A-158C may be referred to as a surgical robotic arm or a robotic surgical arm 158.

The robotic patient-side system 152 further includes a base 202 from which the robotic surgical instruments 101 may be supported. More specifically, the robotic surgical instruments 101 are each supported by the positioning linkage 156 and the surgical robotic arms 158. The linkage structures may optionally be covered by protective covers or not to minimize the inertia that is manipulated by the servomechanism and the overall weight of robotic patient-side system 152.

The robotic patient-side system 152 generally has dimensions suitable for transporting between operating rooms. It typically can fit through standard operating room doors and onto standard hospital elevators. The robotic patient-side system 152 may have a weight and a wheel (or other transportation) system that allows the cart to be positioned adjacent to an operating table by a single attendant. The robotic patient-side system 152 may be sufficiently stable during transport to avoid tipping and to easily withstand overturning moments that may be imposed at the ends of the robotic arms during use.

Robotic Surgical Arms with Multiple Control Straps

Figure 3:
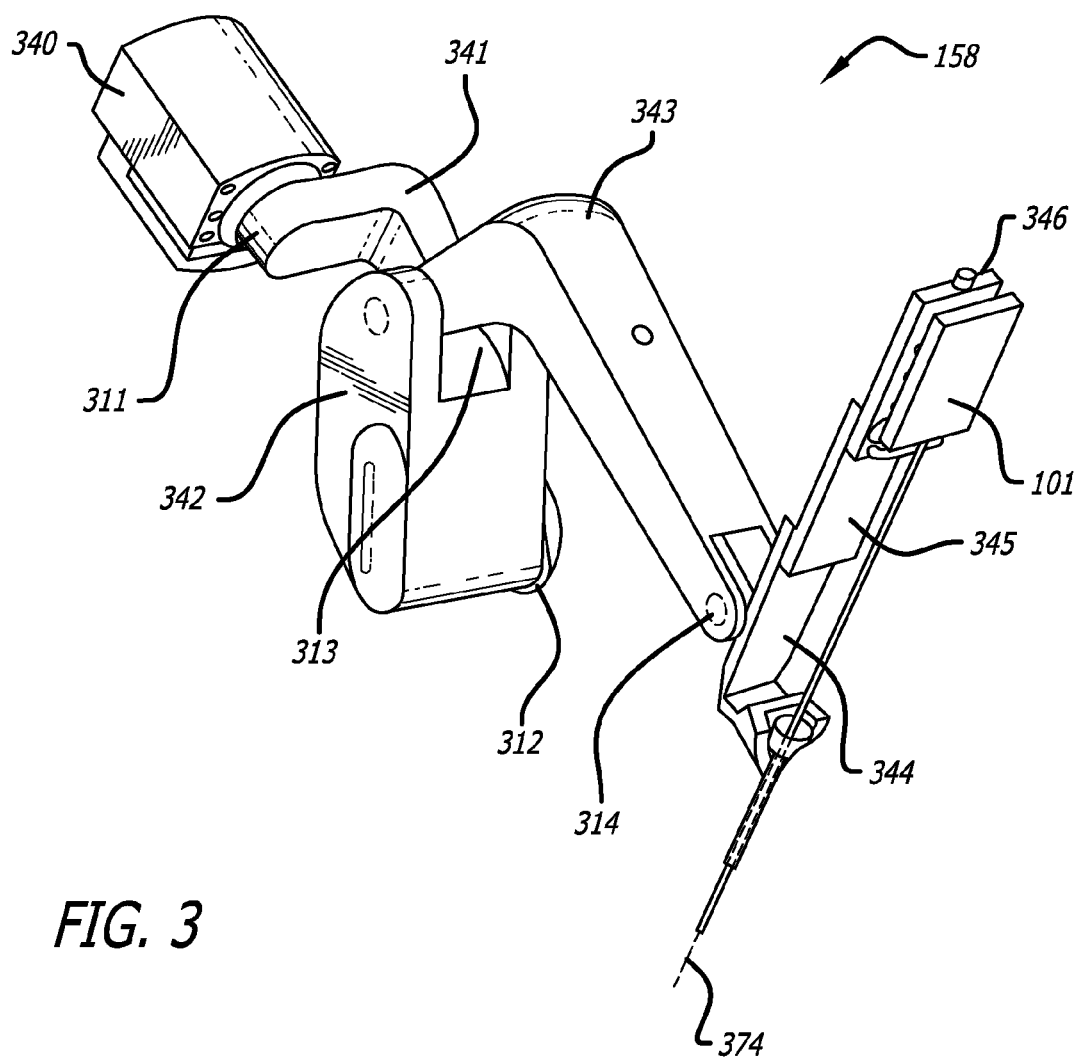
FIG. 3 is a perspective view of a surgical robotic arm for use as a patient side manipulator or endoscopic camera manipulator.

Referring now to FIG. 3, a perspective view of a robotic surgical arm 158 is illustrated. As discussed previously, the robotic surgical arms 158 are for coupling to robotic surgical tools 101. The robotic surgical arms 158 each include serial links 341-344 pivotally coupled in series at joints 312-314 near respective ends of the links. The first link (Link 1) 341 is pivotally coupled to a drive mount 340 at a first joint 311 near a first end and the second link (Link 2) 342 at the second joint 312 near a second end. The third link (Link 3) 343 is pivotally coupled to the second link 342 near a first end and pivotally coupled to the fourth link (Link 4) 344 near a second end. Generally, the fourth link is substantially in parallel to the insertion axis 374 of the robotic surgical tool. A fifth link (Link 5) 345 is slidingly coupled to the fourth link 344. A sixth link (Link 6) 346 is slidingly coupled to the fifth link 345. Various types of surgical tools 428 couple to the sixth link 346.

The robotic surgical arms 158 include the mounting base or drive mount 340 that allows them to be mounted and supported by set-up arms/joints 156 and 156' of a cart mount, ceiling mount, floor/pedestal mount, or other mounting surface of a patient side system 152. The mounting base or drive mount 340 is pivotally coupled to the first link 341 to yaw the links of the robotic surgical arm about a yaw axis.

The third link 343 has a bend with respect to the pitch axis that is offset from center. The bend in the third link allows the links 342-344 to be brought more closely together and provide a greater range of pitch in the robotic arm. The bend may be formed at different angles depending upon the lengths and shapes of the other links. With the bend, the third link is shaped somewhat like a hockey stick. The first link 341 also has a bend with respect to the pitch axis. Thus, the third link 343 may alternately be referred to as a bent link, the main bent link, or a hockey stick shaped link. With no yaw, the second link 342 provides a vertical motion in the third link 343. Additionally, the second link 342 may house the motor to drive the linkage of the arm. Thus, the second link 342 may also be referred to as the vertical link or the drive link. As the fourth link 344 typically slidingly holds the robotic surgical tool or the endoscopic camera through the fifth and sixth links, the fourth link may also be referred to as the instrument holder link.

Figure 4:
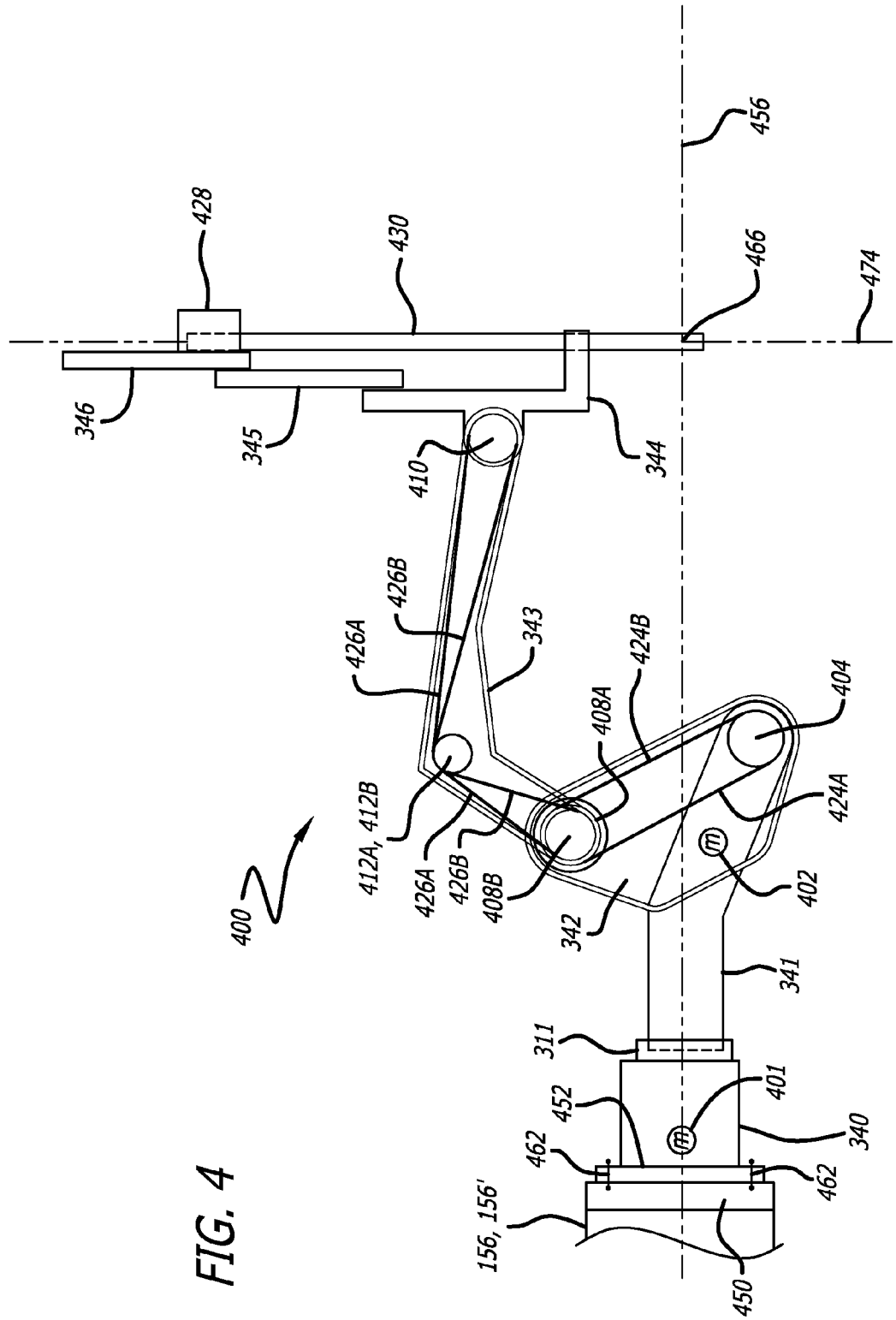
FIG. 4 is a schematic side view of an exemplary multi-strap drive train in a surgical robotic arm.

Referring now to FIG. 4, a schematic diagram of a strap drive train as an exemplary embodiment of a robotic surgical arm 400 is illustrated. The strap drive train of the robotic surgical arm 400 may be used in the structure of the arms 158A-158C illustrated in FIGS. 1, 2, and 3 in one embodiment of the invention. The strap drive train of the robotic surgical arm 400 drives the weight or load of the robotic arm itself from the links, joints, pulleys, cables, straps, etc. and the load that may be placed on it by the surgical tool in the surgical site. Without the strap drive train, the robotic surgical arm 400 would collapse and a remote center point 466 would not be maintained. Besides straps/belts/bands and pulleys for a drive train, other types of drive train means may be used in the structure of the robotic surgical arms 158A-158C illustrated in FIGS. 1, 2, and 3, such as a continuous toothed timing belt with a timing gear, mechanical cables (one or more in parallel together) with shouldered pulleys, chains with sprockets, continuous perforated metal tapes around pulleys with bull nose pins, as well as other like drive train.

While the robotic surgical arm 400 includes the links and joints described previously herein with reference to FIG. 3, the strap drive train of the robotic surgical arm 400 includes six pulleys 404, 408A, 408B, 410, 412A, 412B and four straps 424A, 424B, 426A, 426B in one embodiment of the invention. The six pulleys 404, 408A, 408B, 410, 412A, 412B and four straps 424A, 424B, 426A, 426B are configured with the links and joints of the robotic surgical arm 400 to constrain the motion of the shaft 430 of the surgical tool or endoscopic camera relative to the center of rotation 466.

In the second link 342, straps 424A-624B are coupled between pulleys 404 and 408A. In the third link 343, the straps 426A-626B are coupled between pulleys 408B,610 and ride over the idler pulleys 412A,612B, respectively, in one embodiment of the invention. At the second joint, pulley 404 is rigidly coupled to the first link 341. At the third joint 313, pulley 408A is rigidly coupled to the third link 343. At the third joint 313, pulley 408B is rigidly coupled to the second link 342. At the fourth joint 314, pulley 410 is rigidly coupled to the fourth link 344.

It will be appreciated that the term pulley 404, 408A, 408B, 410, 412A, 412B, 412' can include wheels, gears, sprockets, pulleys with bullnose pins, and the like. Furthermore while two straps 426A,426B are shown being used in the third link 343 between pulleys 410 and 408B, three straps may be used in another embodiment of the invention. In this case, strap 426A is used between pulleys 410 and 408B, a second strap is used between pulley 408B and a pulley 412 (pulley 412A, 412B coupled together), and a third strap is used between pulley 412 and pulley 410.

The mounting base or drive mount 340 includes a motor 401 to yaw the robotic arm 400 about the axis 456 illustrated in FIG. 4.

Slideable Electro-Mechanical Interfaces

In FIG. 4, the mounting base or drive mount 340 of the surgical robotic arm 400 includes electrical and mechanical connectors 452 to mate with electrical and mechanical connectors 450 in a connector portion of a set-up joint of the set up arm 156,156'. Additionally, fasteners 462 (such as bolts) may be used to rigidly couple the robotic surgical arm 400 to the set up arm 156,156'. Alternatively, a lever arm may be used to lock and unlock the arm 400 from the arms 156,156' to quickly mount and dismount the robotic surgical arm from the patient side system. Including a slideable electro-mechanical interface between the surgical robotic arm 400 and the set up arm 156,156' can also assist in quickly mounting and dismounting a robotic surgical arm from a patient side system.

Figure 5A:
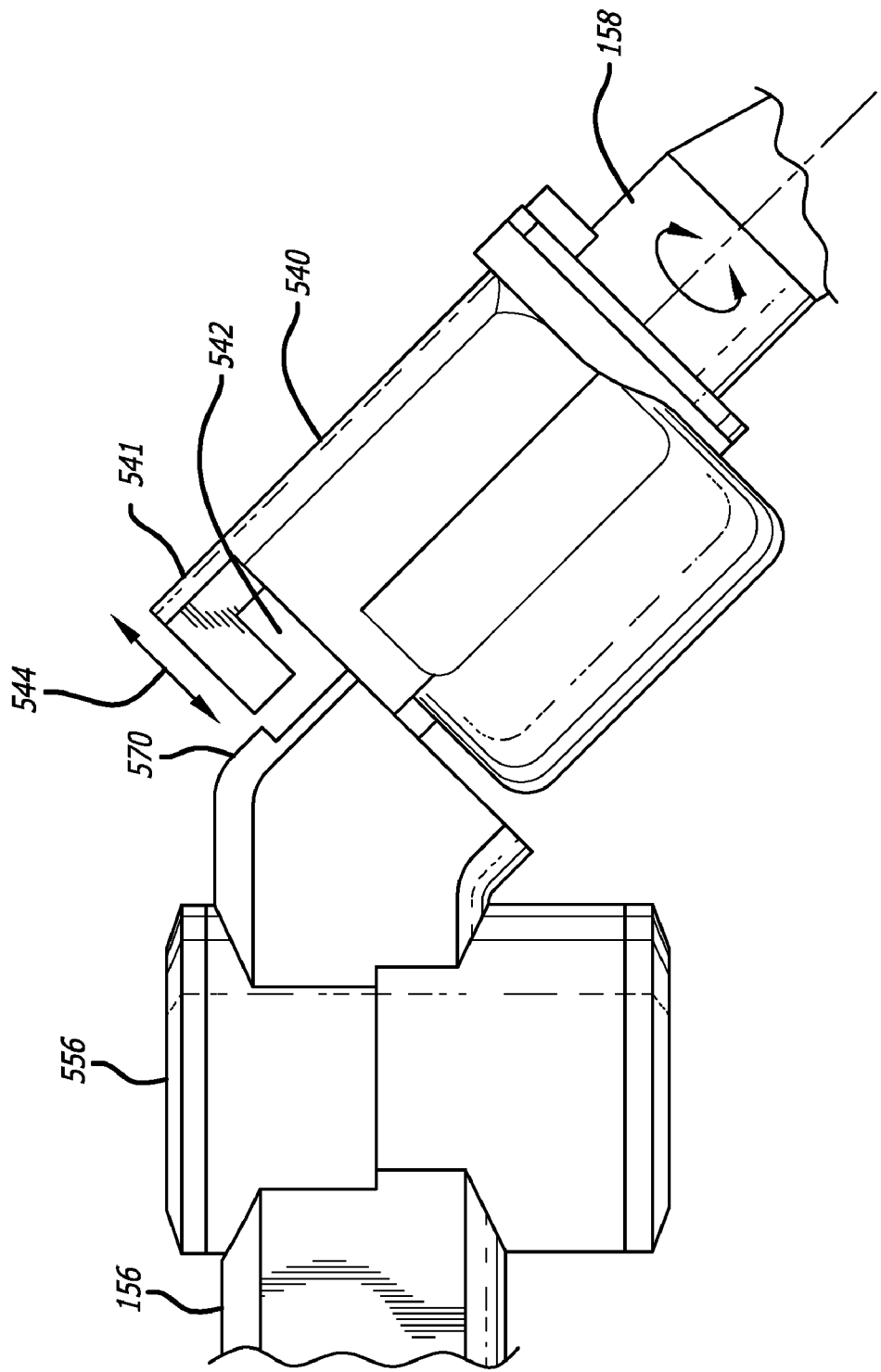
FIGS. 5A-5B are a side view and a cross-section view of a portion of the surgical robotic arm shown in FIG. 3 illustrated as mounting to a set-up joint of the robotic patient-side system of FIG. 2.
Figure 5B:
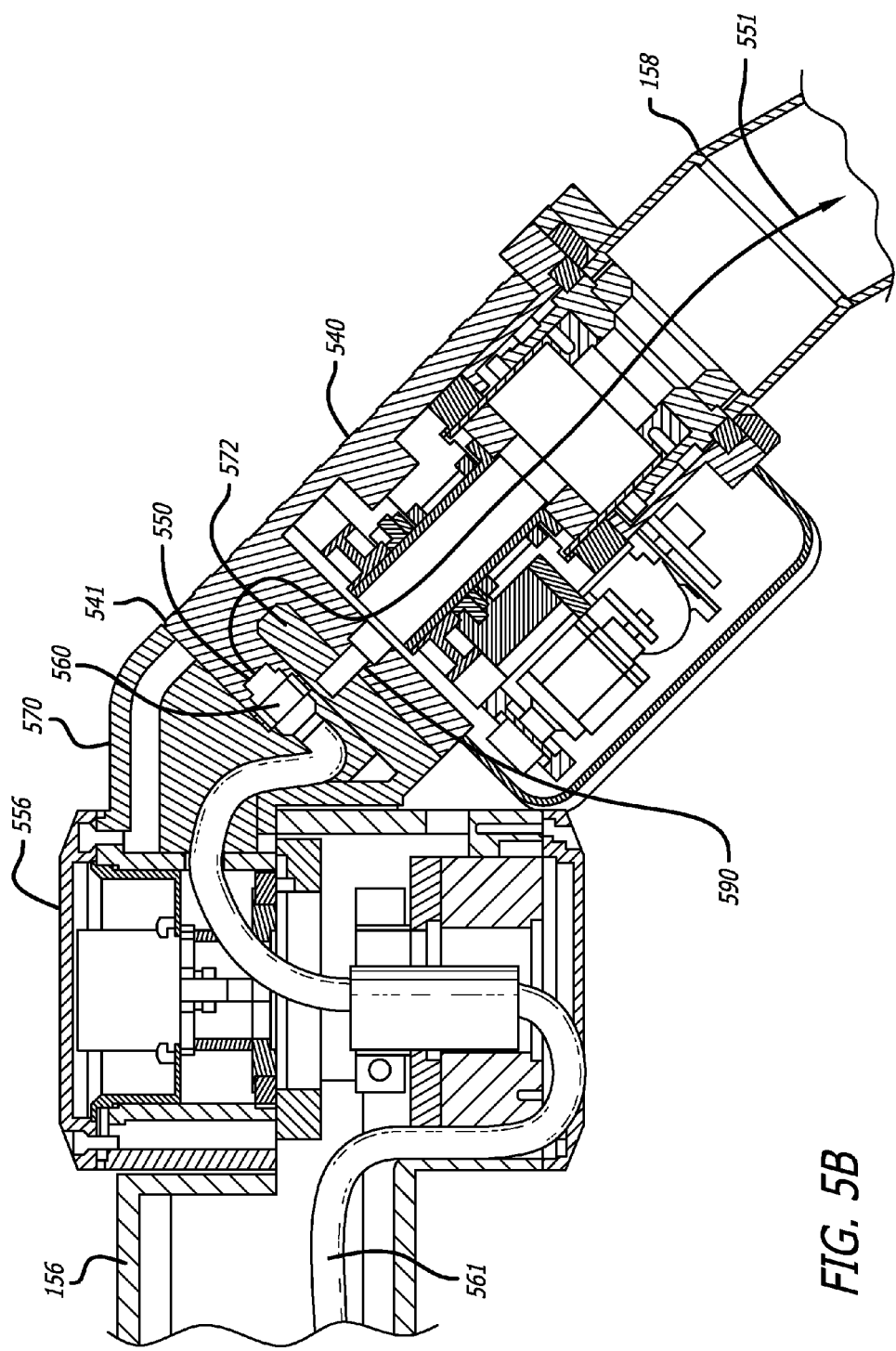

Referring now to FIGS. 5A-5B, a side view and a sectional view of a surgical robotic arm (SRA) portion 540 of a surgical robotic arm 158 and a set-up joint (SUJ) portion 556 of a set up arm 156,156' of the robotic patient-side system 152 is shown. Generally, the SRA portion 540 of the surgical robotic arm 158 is mechanically and electrically coupled coincidentally to the SUJ portion 556 of the set up arm 156 as shown in FIG. 5A. That is, the SRA portion 540 and the SUJ portion 556 mechanically and electrically couple together substantially simultaneously to form a joint.

The SRA portion 540 is adapted for mechanically coupling to the SUJ portion 556 of the set up arm. A connector section 541 of the SRA portion 540 can be slid into and out of a connector portion 570 of the SUJ portion 556 as illustrated by double headed arrow 544 in FIG. 5A. The connector section 541 of the SRA portion 540 has a slot 542 for receiving a tab 572 of the SUJ portion 556. The SUJ portion 556 may also be referred to herein simply as a set-up joint 556. The SRA portion 540 may also be referred to herein previously as a drive mount 340 or a mounting base 340.

As shown in FIG. 5B, the connector section 541 of the SRA portion 540 is adapted for electrically coupling to the connector portion 570 of SUJ portion 556. To do so, the connector portion 570 of SUJ portion 556 includes one or more electrical connectors 560, such as electrical connectors 650A and 650B in FIG. 6 or an electrical connector 1450 in FIG. 14, as described in greater detail in conjunction with FIGS. 6 and 14 below. The connector section 541 of the SRA portion 540 respectively includes one or more electrical connectors 550, such as electrical connectors 750A and 750B shown in FIG. 7 or a single wide electrical connector 1750 shown in FIG. 17, as described in greater detail in conjunction with FIGS. 7 and 17 below.

As the connector section 541 of the SRA portion 540 slides along the connector portion 570 of SUJ portion 556, the electrical connectors 550 and 560 are first aligned together and then electrically and mechanically coupled together. In one embodiment of the invention, the electrical connectors 550 in the SRA portion 540 are fixed in position and the electrical connectors 560 in the SUJ portion 556 are adjustable in position such that they can be aligned to the connectors 550. In an alternate embodiment of the invention, not shown, the electrical connectors 560 in the SUJ portion 556 are fixed in position and the electrical connectors 550 in the SRA portion 540 are adjustable in position such that they can be aligned to the connectors 560.

One or more bolts 590, 462, or 900 are used to remove any play between the connector section 541 of the SRA portion 540 and the connector portion 570 of SUJ portion 556 by forcing surface to surface contact between each. In the surgical robotic arm 158, one or more cables 551 are used to couple data signals, control signals, power, and ground from the connectors 550 to the electrical system of the surgical robotic arm 158. In the set up arm 156, one or more cables 561 are used to couple data signals, control signals, power, and ground from the connectors 560 to the electrical system of the patient side system 152.

Figure 6:
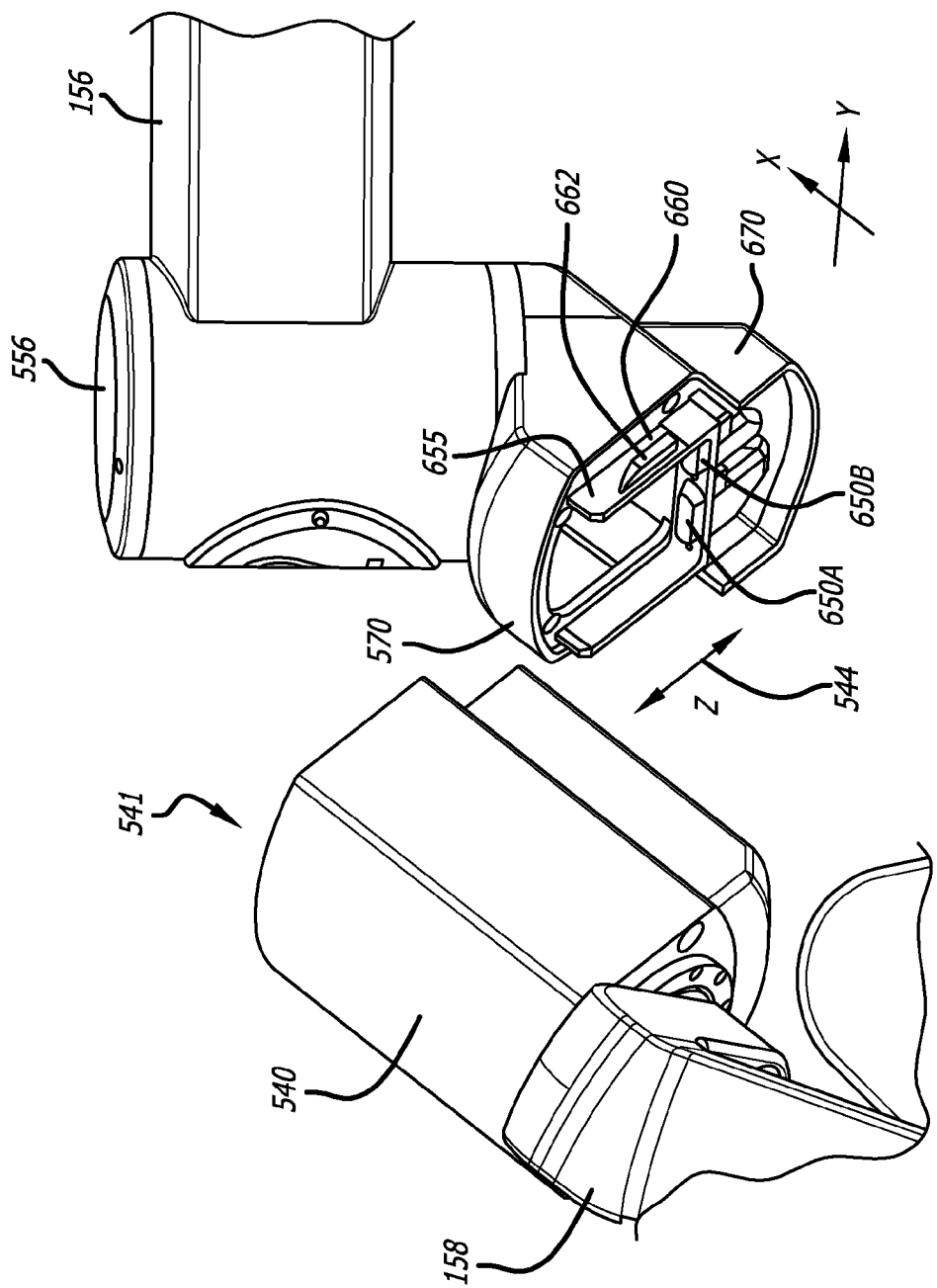
FIGS. 6-9 are perspective views illustrating the mounting and dismounting of the robotic surgical arm of FIG. 3 with a set-up arm of the robotic patient-side system of FIG. 2.
Figure 7:
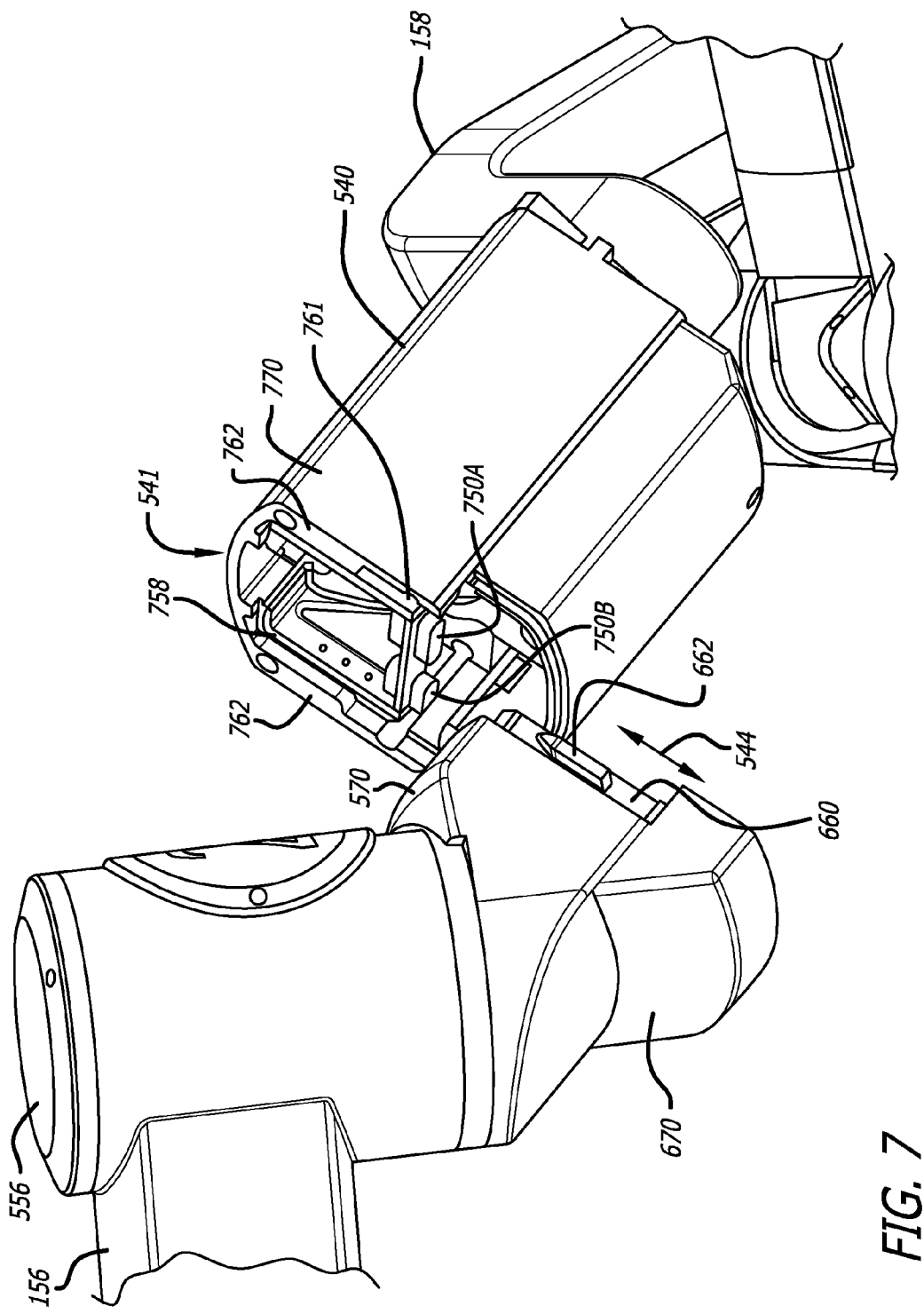
Figure 8:
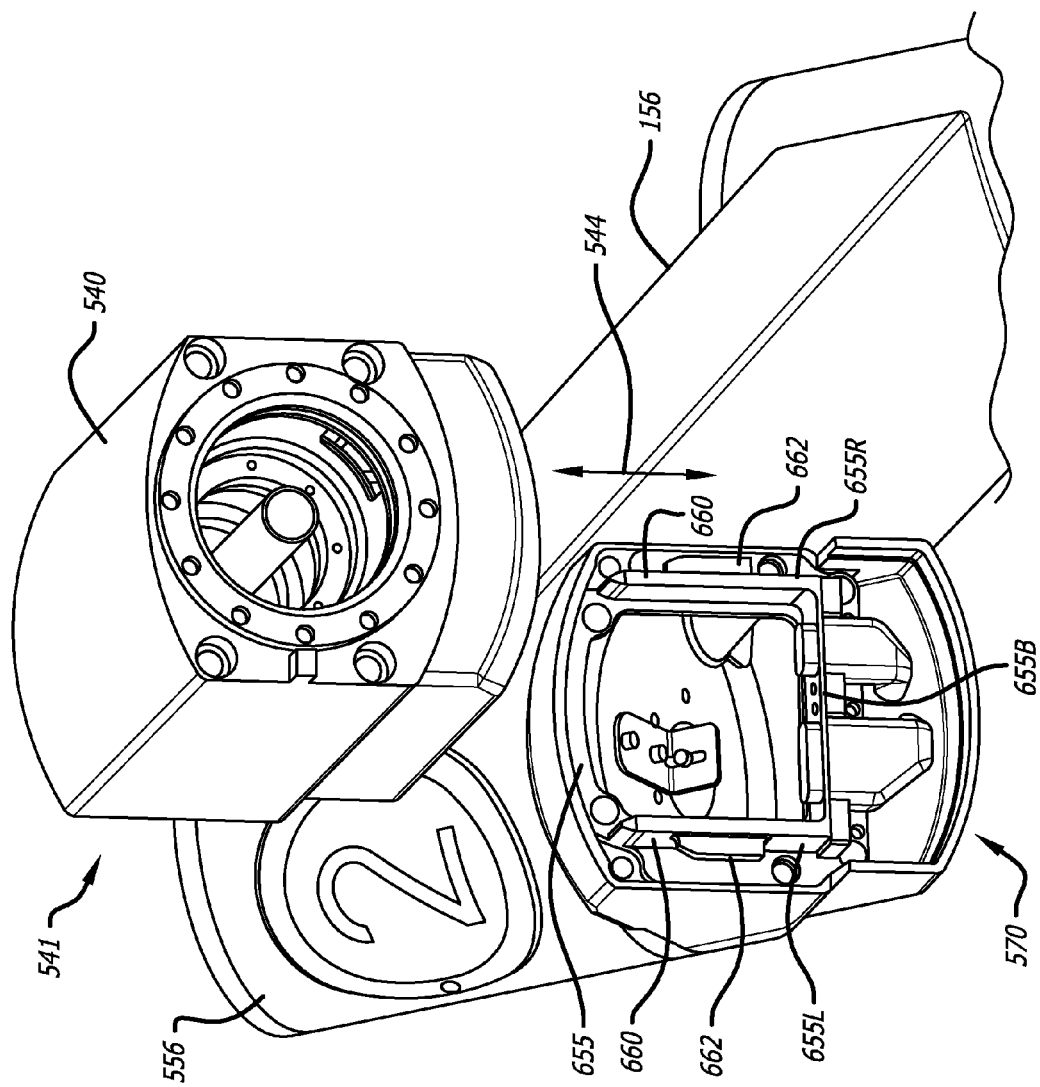
Figure 9:
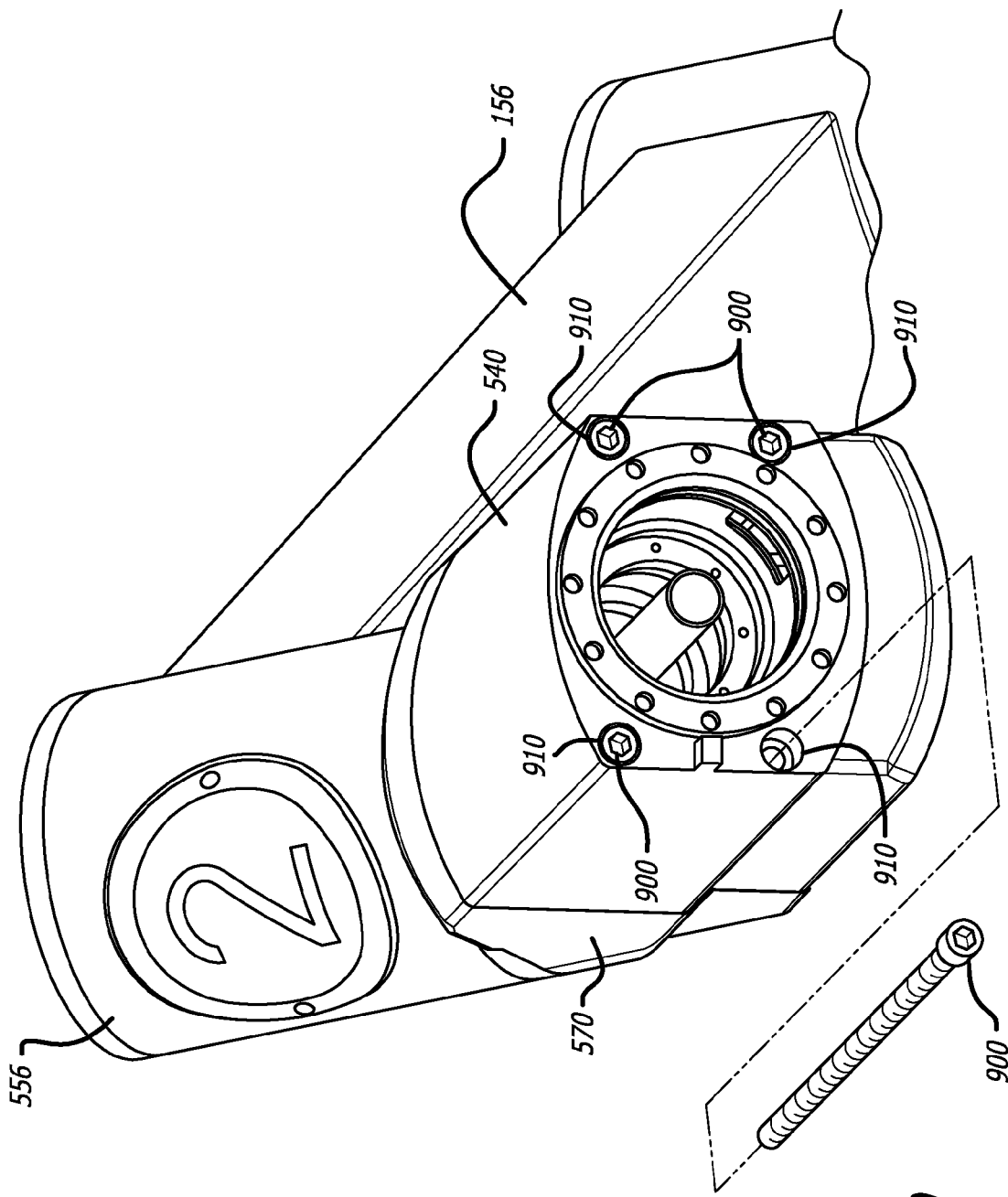

Referring now to FIGS. 6-9, detailed perspective views of the SRA portion 540 of the robotic surgical arm 158 and the SUJ portion 556 of the set up arm 156 are illustrated to better show how they slide apart and together. In this exemplary embodiment of the invention, the connector section of the SRA portion 540 is adapted to connect to the connector portion 570 of the SUJ portion 556. In FIGS. 6-9, magnified views are provided that do not show the entire surgical robotic arm 158 or the entire set-up arm 156. In FIGS. 8-9, portions of the surgical robotic arm 158 have been removed (e.g., disassembled) to better illustrate the connector section thereof and the connector portion of the set-up joint.

As shown in the right perspective view of FIG. 6, the connector portion 570 includes a pair of electrical connectors 650A and 650B, and a mounting bracket 655. The connector portion 570 further includes a housing 670 that is coupled to and may be considered a part of the set up joint 556 of the set up arm.

In an exemplary embodiment, electrical connectors 650A and 650B are D-subminiature (D-SUB) electrical connectors, although any connector with a flange mount can also be used. A D-sub electrical connector has two or more parallel rows of pins or sockets surrounded by a D-shaped metal shield. The D-shaped metal shield provides screening against electromagnetic interference and assures correct orientation. The D-shaped metal shield may be coupled to the overall screen of the cable if used, creating an electrically continuous screen covering the whole cable and connector system. A male D-sub electrical connector has pin contacts. A female D-sub electrical connector has socket contacts. The D-shaped shield of the female D-sub electrical connector fits tightly inside the D-shaped shield of the male D-sub electrical connector. D-sub electrical connectors are further described in international standard DIN 41652 by the German Institute for Standardization.

Electrical connectors 650A and 650B include pins for carrying control and data signals, power and ground. Electrical connector 650B provides shielding for its signal pins from electromagnetic interferences, such as those from the electrical connector 650A that may provide power and ground to electric motors. Chassis ground may be made through the mechanical interface (e.g., flanges, tabs, rails, and bolts) or additional ground strapping. As described in greater detail below, the electrical connectors 650A and 650B may be referred to as "floating" electrical connectors.

The mounting bracket 655 includes mechanical mounting rails 660 with guide tabs 662 for mechanically coupling to the SRA portion 540, such as by receiving the opposing guide rails 761 in the SRA portion 540 (FIG. 7) along the Z-axis 544, as shown in FIG. 6. The mounting bracket 655 is bolted to the housing 670 of the SUJ portion 556 by a plurality of bolts. In this manner, the mounting bracket 655 can be detached to replace worn parts or if it has worn out mounting rails 660 or guide tabs 662 it can be readily replaced. While the electrical connectors 650A and 650B are allowed to move or float in two directions (X-axis and Y-axis), the mounting bracket 655 supports the electrical connectors 650A and 650B along the Z-axis 544 so there is little movement in the Z-axis direction in order to mate with electrical connectors in the surgical robotic arm 158. The Z-axis 544 is parallel to the axis of the pins/sockets of the electrical connectors 650A-650B while the X-axis and the Y-axis are perpendicular to the axis of the pins/sockets of the electrical connectors 650A-650B.

Referring now to the left perspective view of FIG. 7, the SRA portion 540 includes a pair of electrical connectors 750A and 750B to mate respectively with the electrical connectors 650A and 650B of the set up joint 556. The SRA portion 540 further includes a housing 770 that forms a pair of left and right flanges 762 and a pair of left and right guide slots 761 at the connector section end 541. The flanges 762 on each side initially engage a top portion the mounting rails 660 and slide along the mounting rails 660 of the SUJ portion 556. The guide slots 761 then slide along over the guide tabs 662 of the SUJ portion 556 and finally mate or catch behind the flanges 762 of the SRA portions 540. The final mating of the guide tabs 662 with the flanges 762 reduces the pivoting of the SRA portion 540 away from the SUJ portion 556.

The SRA portion 540 further includes a mounting bracket 758 bolted to the housing 770 by a plurality of bolts. The mounting bracket 758 supports the electrical connectors 750A and 750B in a fixed position (X-axis, Y-axis, Z-axis) with respect to the SRA portion 540 in one embodiment of the invention. That is, with the electrical connectors 650A-650B being able to float, the electrical connectors 750A and 750B can be held in a fixed position. As the SRA portion 540 is slid onto the SUJ portion 556, floating electrical connectors 650A and 650B in the SUJ portion 556 are respectively aligned with its pins and mate with the sockets of the electrical connectors 750A and 750B in the SRA portion 540 coincidentally with the final mating of the guide tabs 662 with the flanges 762 of the housing 770. With the mounting bracket bolted to the housing 770, it can be readily detached to allow worn parts to be replaced.

Referring now to FIG. 8, the mounting bracket 655 includes a left side 655L, a right side 655R, and a base 655B. The left mounting rail 660 is formed in the left side 655L with the left guide tab 662. The right mounting rail 660 is formed in the right side 655R with the right guide tab 662. The base 655B of the mounting bracket 655 includes the openings 1008A-1008B.

Referring now to FIG. 9, another perspective view of the robotic surgical arms 158A and 158C is illustrated. As shown in FIG. 9, SRA portion 540 includes a plurality of holes 910, such as four holes 910, for receiving of a plurality of fasteners 900, such as four fasteners 900, such as bolts, to rigidly couple the SRA portion 540 to the rest of the surgical arms 158A and 158C. In an exemplary embodiment of the invention, the SUJ portion 556 remains fixed, while the SRA portion 540 is lifted onto the SUJ portion 556. As illustrated in FIG. 7, the opposing guide flanges 762 of the SRA portion 540 slide into the mounting rails 660 of the SUJ portion 556.

Floating Electrical Connectors

In a first embodiment of the invention (FIGS. 10, 11A-11B), electrical connectors 650A and 650B independently float from each other within sliding pockets 1080A and 1080B, respectively.

In a second embodiment of the invention (FIG. 14A), electrical connectors 1401A and 1401B also float independently but require some extra space between the connectors. The electrical connectors 1401A and 1401B are allowed to move by means of floating bushings 1410.

In a third embodiment of the invention (FIG. 14B), a single electrical connector 1450 is a floating electrical connector, which is allowed to move by means of floating bushings 1410.

Figure 12:
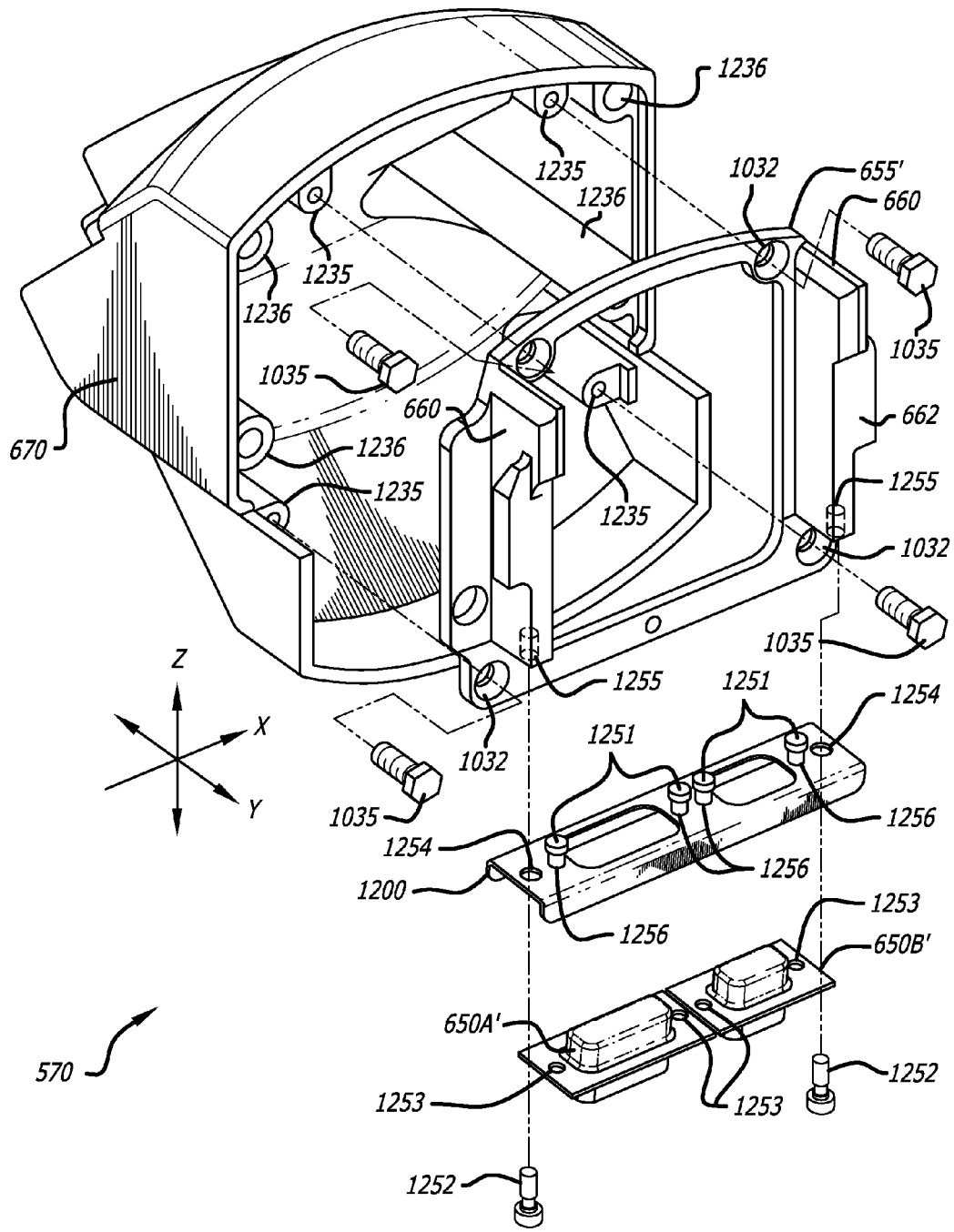
FIG. 12 is an exploded perspective view of alternate exemplary embodiment of the connector portion shown in FIGS. 6-11B
Figure 13A:
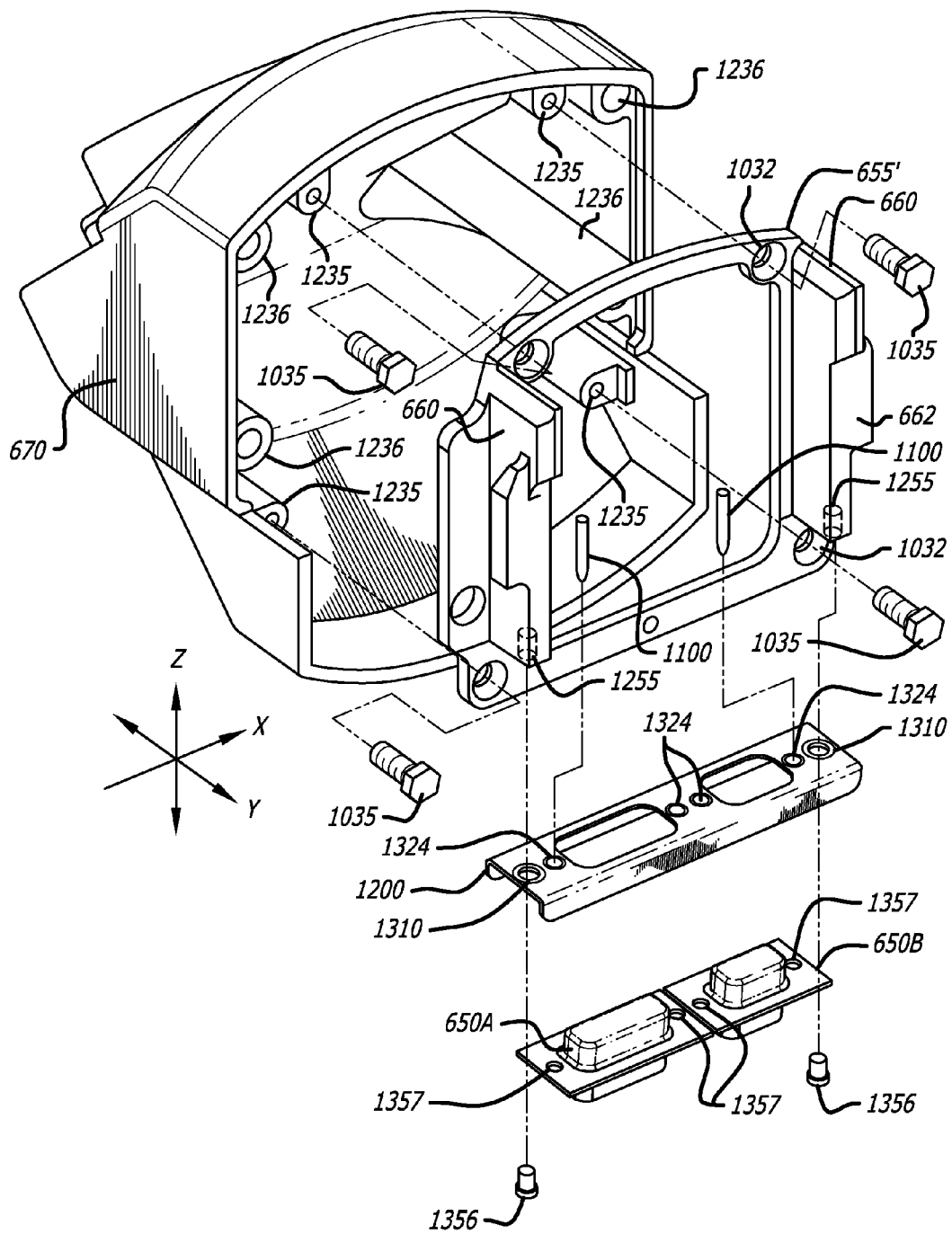
FIG. 13A is an exploded perspective view of alternate exemplary embodiment of the connector portion shown in FIG. 12.
Figure 13B:
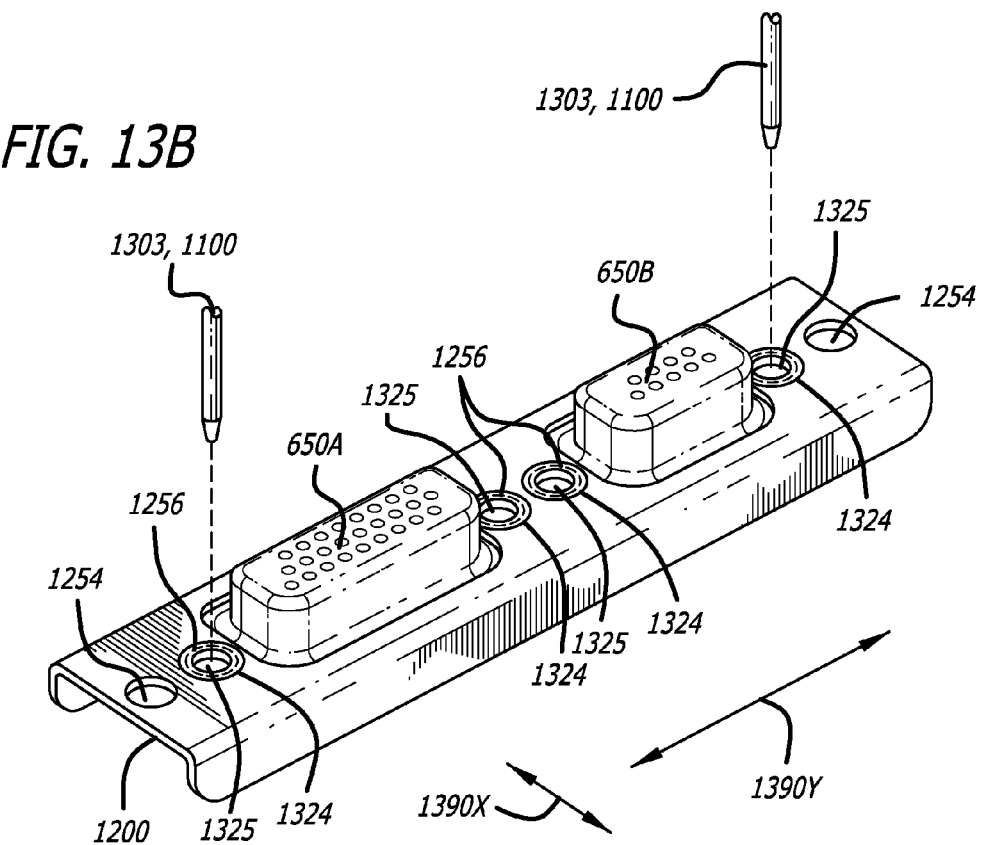
FIG. 13B is a magnified perspective view of the floating electrical connectors of FIG. 13A.

In a fourth embodiment of the invention (FIG. 12) and a fifth embodiment of the invention (FIGS. 13A-13B), electrical connectors 650A'-650B' and 650A-650B float together coupled to a floating bracket 1200, which is allowed to move by means of short shoulder screws 1252 (FIG. 12) or two "floating" bushings 1310 (FIGS. 13A-13B). The short shoulder screws 1252 and floating bushings 1310 allow a very small amount of motion in the axial direction but sufficient motion in the perpendicular plane to account for positional mismatch of the electrical connectors 650A'-650B' and 650A-650B with their mating electrical connectors 750A-750B. In the case of short shoulder screws 1252 (FIG. 12), no guide pins are used to align the floating bracket 1200 or the electrical connectors. Thus, the amount of misalignment tolerated where the electrical connectors can still engage is limited. In the case of two "floating" bushings 1310 (FIGS. 13A-13B), guide pins are used to align the floating bracket and the electrical connectors coupled thereto such that a greater misalignment is tolerated.

Figure 10:
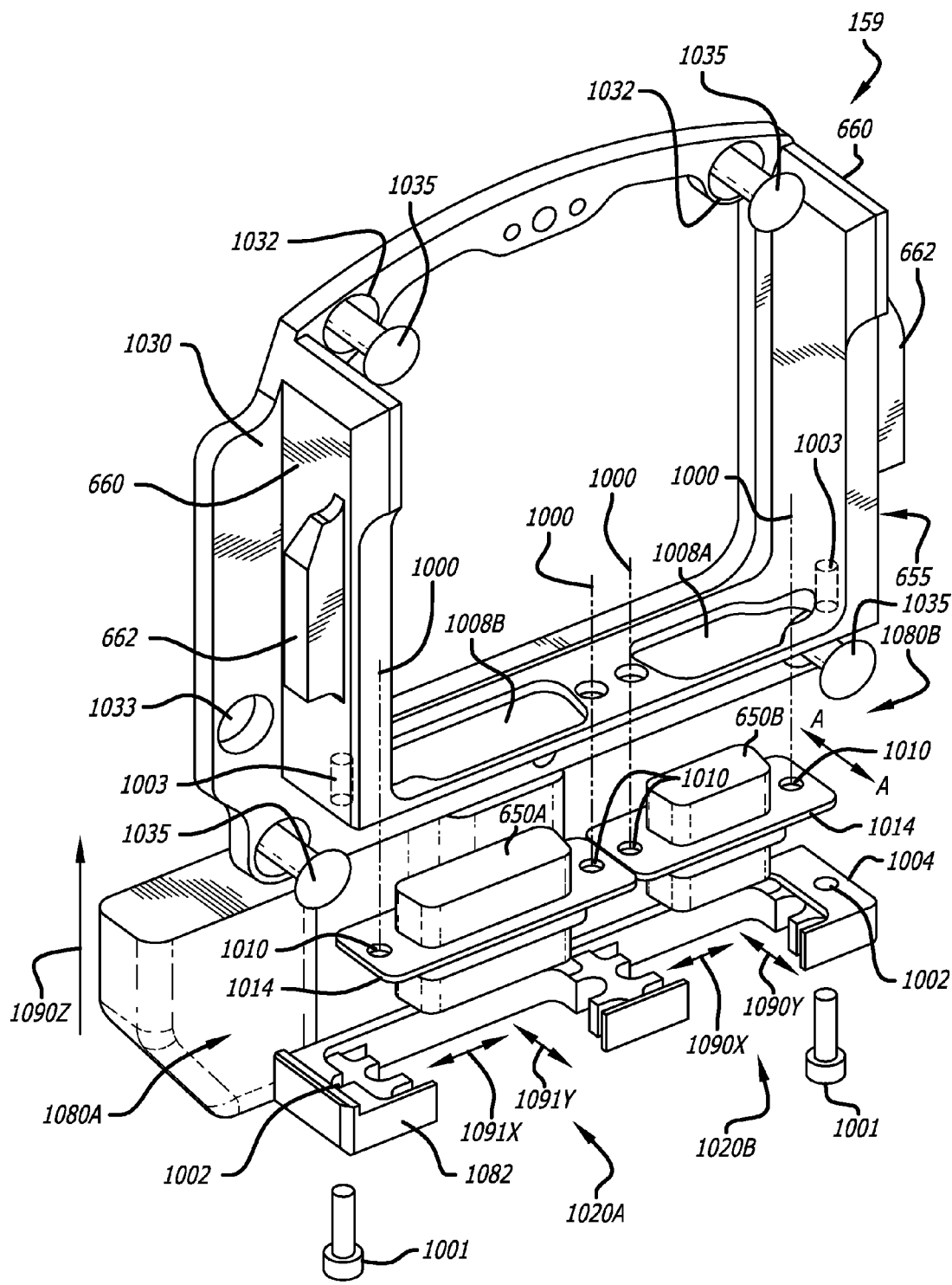
FIG. 10 is an exploded perspective view of an exemplary connector portion of the robotic surgical arm of FIG. 3.

Referring now to FIG. 10 and the first embodiment of the invention, an exploded perspective view of the connector portion 570 is shown. As shown in FIG. 10, a pair of electrical connectors 650A and 650B are adapted to be received by the openings in the mounting bracket 655, such as via openings 1008B and 1008A, respectively. A capture plate 1004, having U-shaped openings 1020A and 1020B, is coupled to the mounting bracket 655 to restrict the motion of the electrical connectors 650A and 650B along the Z-axis, as shown. Both connectors 650A and 650B, however, are capable of independently moving (i.e. floating) within the sliding pockets 1080A and 1080B formed by the capture plate 1004 including its locating surface 1082 and the bottom of the bracket 655 including openings 1008A and 1008B. Connectors 650A and 650B can move in directions perpendicular to the Z-axis 1090, such as in the direction shown by arrows 1091X, 1091Y and 1090X, 1090Y, respectively, which respectively correspond to the X and Y axes in the Cartesian coordinate system.

The capture plate 1004 is coupled to the mounting bracket 655 by way of a pair of screws 1001. The pair of screws 1001 is inserted into a pair of holes 1002 in the capture plate 1004 that allow the threaded shaft of the screws to pass but not the screw heads. The threaded shaft of the screws 1001 are then screwed into a pair of threaded screw holes 1003 in the base of the mounting bracket 655 to secure the capture plate 1004 thereto.

Referring now to FIGS. 8 and 10, to couple the mounting bracket 655 to the housing 670 of the connector portion 570 of the set-up joint 556, the mounting bracket 655 further includes a plurality of openings 1032 in a mounting flange 1030. The plurality of openings 1032 in a mounting flange 1030 allow the passage of a cylindrical portion of a plurality of threaded bolts 1035, but for the head of the bolts. One pair of openings are spaced apart in the mounting bracket 655 and located near a top edge of a mounting flange 1030 and a second pair of spaced apart openings 1032 are located near a bottom edge of the mounting flange 1030. The housing 670 includes a plurality of threaded bolt holes 1235 to receive the plurality of threaded bolts 1035 so that the mounting bracket 655 may be tightly coupled to the housing 670.

The mounting bracket 655 further includes a pair of openings 1033 in the mounting flange 1030 to allow the passage of a cylindrical portion of the plurality of threaded bolts 900, but for the head of the bolts. That is, the pair of openings 1033 in the mounting flange 1030 align with a pair of the openings 910 in the SRA portion 540. The housing 670 includes a plurality of threaded bolt holes 1235 to receive the plurality of threaded bolts 900 so that the SRA portion 540 of the surgical robotic arm may be tightly coupled to the connector portion 570 of the set-up joint 556.

As described in conjunction with FIGS. 11A-11B below, guide pins 1100 inserted into guide pin holes 1000 of the mounting bracket 655 control the range of movement of each of the electrical connectors 650A and 650B. In an exemplary embodiment, two of the four guide pins 1100 are couple into a pair of connector openings or holes 1010 in each of the electrical connectors 650A and 650B to align each of the electrical connectors 650A and 650B with the fixed connectors 750A and 750B (shown in FIG. 15), respectively, in the SRA portion 540. A pair of the guide pin holes 1000 may overlap into the openings 1008A-1008B for the electrical connectors. The use of independently floating electrical connectors 650A and 650B in the SUJ portion 556 makes it easier for the fixed connectors 750A and 750B in the SRA portion 540 to electrically align with the floating electrical connectors 650A and 650B.

Referring now to FIG. 11A, a side sectional view of the connector portion 570 taken along the line A-A (through the alignment pin) in FIG. 10 is shown. FIG. 11B is a magnified side sectional view of the electrical connector mounted in a sliding pocket. As shown in FIGS. 11A and 11B, the guide pin 1100 allows for a floating movement of the electrical connectors 650A and 650B such as a positive float 1101 and a negative float 1102. In one embodiment of the invention, the positive float 1101 and the negative float 1102 in one direction is plus or minus 0.015 inches, for a total of 0.03 inches. In an exemplary embodiment, the amount of connector float from its nominal/centered position (distance A) is at least as large as the maximum mechanical misalignment of the mating connectors due to all mechanical tolerances (distance B). In addition, the misalignment tolerated at which the tapered pin 1100 can still engage the connector hole 1010 is at least as large as the sum of distance A and distance B.

The size and shape of the sliding pockets 1080A-1080B are designed to constrain a flange 1105 of an electrical connector, such as electrical connectors 650A and 650B, in a plane, keeping it parallel to the capture flange 1104 of the capture plate 1004 and allow them to align with the fixed connectors 750A and 750B (shown in FIG. 15), respectively. The size and shape of the sliding pockets 1080A-1080B are also designed to allow the connectors 650A-650B to translate with two degrees of freedom ("floating" in a plane) so that they can be guided and aligned with the fixed connectors 750A-750B using the tapered guide pins 1100. With the capture plate 1004 coupled to the base of the mounting bracket 655, the sliding pockets 1080A-1080B for the connectors 650A-650B are respectively formed by the openings 1008A-1008B in the mounting bracket and the U shaped openings 1020A-1020B. A pair of guide holes 1000 may merge into the openings 1008A-1008B and be considered as part of the sliding pockets 1080A-1080B. The connector flanges 1105 (see FIG. 11A) are captured in the sliding pockets 1080A-1080B between a bottom surface of the bottom side 655B of the bracket 655 (see FIG. 8) and a top recessed locating surface 1082 of the capture plate 1004. The connectors 650A-650B are allowed to translate with two degrees of freedom within the top recessed locating surface 1082 of the capture plate 1004.

Referring now to FIG. 12, the fourth embodiment of the invention, an exploded perspective view of an alternate embodiment of the connector portion 570 of FIG. 10 is shown. In this alternate embodiment, modified electrical connectors 650A' and 650B' are rigidly attached to a common floating bracket 1200 via a first plurality of fasteners 1251 that may be screwed into threaded holes 1253 on the flanges of the electrical connectors.

The modified electrical connectors 650A' and 650B', if female connectors, have shielding that is slightly flared outward, referred to as flared shielding, to mate with male connectors that are modified having shielding that is slightly tapered inward, referred to as tapered shielding. Alternatively, if the modified electrical connectors 650A' and 650B' are male connectors, they have tapered shielding that is slightly tapered inward to mate with female connectors that are modified having flared shielding that is slightly flared outward. As a result, the connectors 650A'-650B', by design, will tolerate some small amount of misalignment. With the modified electrical connectors 650A' and 650B', no guide pin from the connector section 541 of the SRA portion 540 is used to align the electrical connectors or the common floating bracket of the connector portion 570 of the SUJ.

A second plurality of fasteners—such as short shoulder screws 1252 as illustrated or screws 1356 inserted through floating bushings 1310 in the floating bracket 1200 (shown in FIG. 13A)—hold the floating bracket 1200 to the mounting bracket 655' in the Z direction while allowing the floating bracket to move a small amount in the X and Y directions. Fasteners 1252 or 1356 extend through the openings 1254 in the floating bracket 1200 and are screwed into threaded holes 1255 in the left and rights sides of the mounting bracket 655'.

With the floating bracket 1200, the mounting bracket 655' is modified slightly from the mounting bracket 655 (see FIG. 8). The mounting bracket 655' includes the left side 655L and the right side 655R but does not have the base portion 655B. Instead, at the bottom of the left side 655L and the right side 655R, are the threaded holes 1255 in the mounting bracket 655'.

Referring now to FIGS. 13A-13B, the fifth embodiment of the invention, an exploded perspective view of an alternate embodiment of the connector portion 570 of FIG. 12 is shown. In this fifth embodiment of the invention, guide pins of the connector section 541 of the SRA portion 540 are used to align the common floating bracket 1200 and the electrical connectors 650A-650B coupled thereto. The mounting bracket 655' and the floating bracket 1200 are similar to those of the fourth embodiment of the invention illustrated in FIG. 12. However, standard electrical connectors 650A-650B may be used instead of the modified connectors 650A'-650B' having the tapered/flared shielding. Additionally, the way the electrical connectors 650A-650B are coupled to the floating bracket 1200 is different.

A plurality of grommets 1324 rigidly couple the electrical connectors 650A-650B to the common floating bracket 1200. The plurality of grommets 1324 align and couple holes 1256 in the common floating bracket 1200 to through holes 1357 in the connector flanges of the connectors 650A-650B. A plurality of floating fasteners—such as short shoulder screws 1252 (illustrated in FIG. 12) or screws 1356 inserted through floating bushings 1310 in the floating bracket as illustrated— hold the floating bracket 1200 to the mounting bracket 655' in the Z direction while the short shoulders of the short should screws and the floating bushings 1310 allow the floating bracket to move a small amount in the X and Y directions. Fasteners 1252 or 1356 extend through the openings 1254 in the floating bracket 1200 and are screwed into threaded holes 1255 in the left and rights sides of the mounting bracket 655'.

In operation, two tapered guide pins 1100 engage the outer most grommet holes in the outermost grommets 1324 to move the floating bracket 1200 and the electrical connectors 650A and 650B into correct alignment with the mating connectors 750A and 750B of the SRA. In contrast, the fourth embodiment of the invention illustrated by FIG. 12B does not require taper guide pins 1100. In both the fourth and fifth embodiments of the invention, the electrical connectors 650A-650B, 650A'-650B' respectively move together as they are both coupled to the floating bracket 1200.

FIG. 13B is an exploded perspective view of the common floating bracket 1200. As shown in FIG. 13B, the top common floating bracket 1200 includes openings 1254 to receive floating bushings 1310 and fasteners 1356 to couple it to the mounting bracket 655'. Each of the holes 1256 in the bracket 1200 receives a small metal grommet 1324 to rigidly fasten the flanges of connectors 650A-650B to the floating bracket 1200 in the fifth embodiment of the invention. In contrast, each of the holes 1256 received a fastener 1251 in the fourth embodiment of the invention to rigidly fasten the flanges of connectors 650A'-650B' to the floating bracket 1200.

Openings in the outer pair of the grommets 1324 are engaged by the alignment posts 1303 or guide pins 1100 in the SRA to move the floating bracket 1200 and the electrical connectors into correct alignment. In this case, the electrical connectors 650A and 650B are floating connectors but float together in common with the bracket 1200, rather then independently as in the embodiment shown in FIG. 10. The bracket 1200 floats such as shown in the direction of arrows 1390× and 1390Y, respectively, which respectively correspond to the X and Y axes in the Cartesian coordinate system.

Figure 14C:
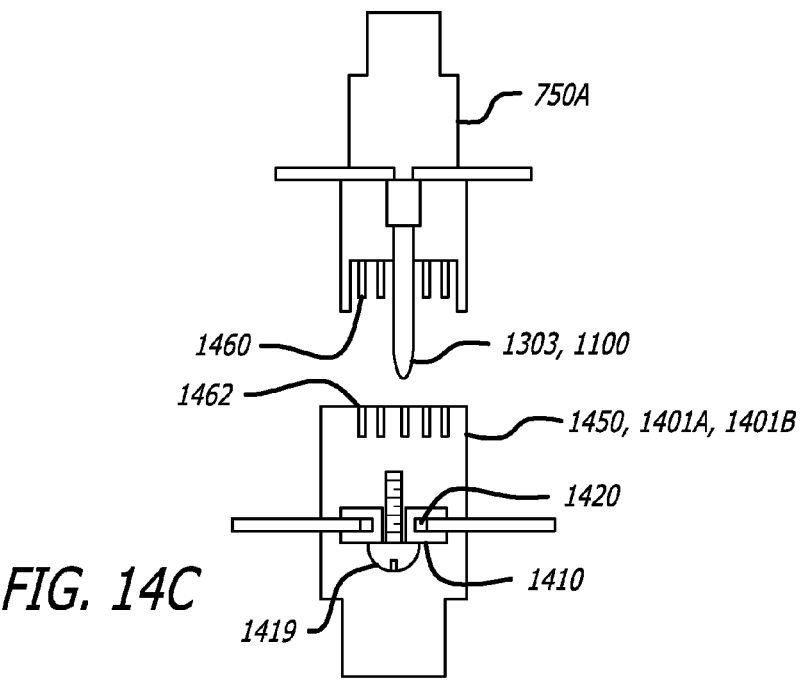
FIG. 14C is a side cross-sectional view of the floating electrical connectors of FIGS. 14A-14B.
Figure 14A:
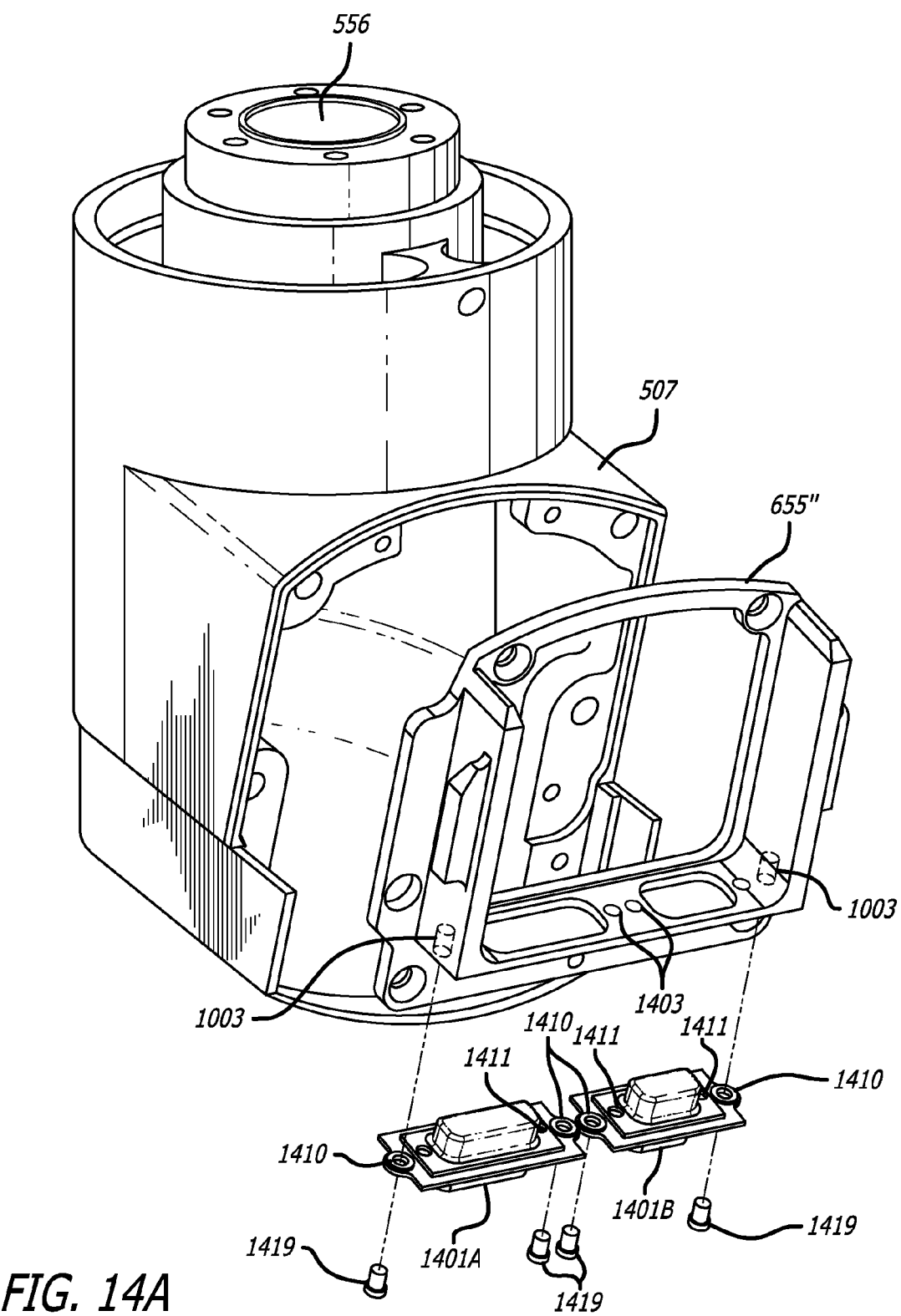
FIG. 14A is an exploded perspective view of a further exemplary embodiment of the invention.

Referring now to FIG. 14A, the second embodiment of the invention, an alternate embodiment of the connector portion 570 of FIG. 10 with electrical connectors 1401A and 1401B is shown. Connectors 1401A and 1401B each contain two floating bushings 1410 and two guide pin holes 1411. These connectors float independently from one another as does the connectors 650A-650B in the preferred embodiment of invention illustrated in FIG. 10. Thus, the electrical connectors 1401A-1401B may also be referred to as floating electrical connectors. However because, in addition to the four guide pin holes 1411, two floating bushings 1410 are required on each connector to moveably couple them to the mounting bracket 655", an extra space between the connectors 1401A-1401B is required. In one embodiment of the invention, the extra space is approximately 0.5 inches.

A plurality of fasteners 1419 are inserted through the opening in the floating bushings 1410 to moveably couple the electrical connectors 1401A-1401B to the bracket 655". The mounting bracket 655" is similar to the mounting bracket 655 but may include threaded holes 1403 to receive the inner fasteners 1419. The outer fasteners 1419 threadingly couple into the threaded holes 1003.

Guide pins or posts 1100, 1303 from the SRA slide into the guide pin holes 1411 in each electrical connector 1401A-1401B. The guide pins or posts inserted into the guide pin holes align the electrical connectors 1401A-1401B independently. The guide pins or posts cause each electrical connector 1401A-1401B to move about its floating bushings 1410 to align with the electrical connectors in the SRA.

Referring now to FIG. 14B, the third embodiment of the invention, an exploded perspective view of an alternate embodiment of the connector portion 570 of the SUJ portion 556 is shown. As shown in FIG. 14B, a single floating electrical connector 1450 is secured to the mounting bracket 1455 via floating bushings 1410. The mounting bracket 1455 is substantially similar to the bracket 655' and lacks the base 655B of the mounting bracket 655.

In this embodiment of the invention, the electrical connector 1450 is a floating electrical connector, which can move in the direction shown by arrows 1490× and 1490Y, which respectively correspond to the X and Y axes in the Cartesian coordinate system. The guide pins 1100 or alignment pins 1303 of a fixed connector, such as fixed connector 1750 illustrated in FIG. 17, engage alignment or connector holes 1411 in the flange of the floating electrical connector 1450.

The floating electrical connector 1450 then moves about its floating bushings 1410 to align with the electrical connector in the SRA.

Referring now to FIG. 14C, a side cross-sectional view of the floating electrical connectors of FIGS. 14A-14B is illustrated with the connector portion of the set up joint aligned to mate with the fixed connector of the robotic surgical arm. FIG. 14C particularly illustrates a cross section view of an exemplary floating bushing 1410 for use with the floating electrical connector, such as electrical connector 1401A-1401B, 1450 illustrated in FIGS. 14A-14B.

The floating bushings 1410 are placed in float bushing openings 1420 of the flanges of the electrical connectors. A fastener 1419 is inserted up through the opening in each of the floating bushings 1410 to thread into holes 1003, 1403. In an exemplary embodiment of the invention, the floating bushing 1410 is of a metallic composition, such as steel.

Guide pin or post 1303, 1100 of a fixed electrical connector, such as fixed electrical connector 750A, engages an alignment or connector hole 1411 (see FIGS. 14A-14B) on the flange of the floating electrical connector 650A. As the electrical connectors are aligned, male conductive pins 1460 may engage female conductive pins 1462 in the connectors or vise versa.

Connector Sections of Surgical Robotic Arms

Figure 15:
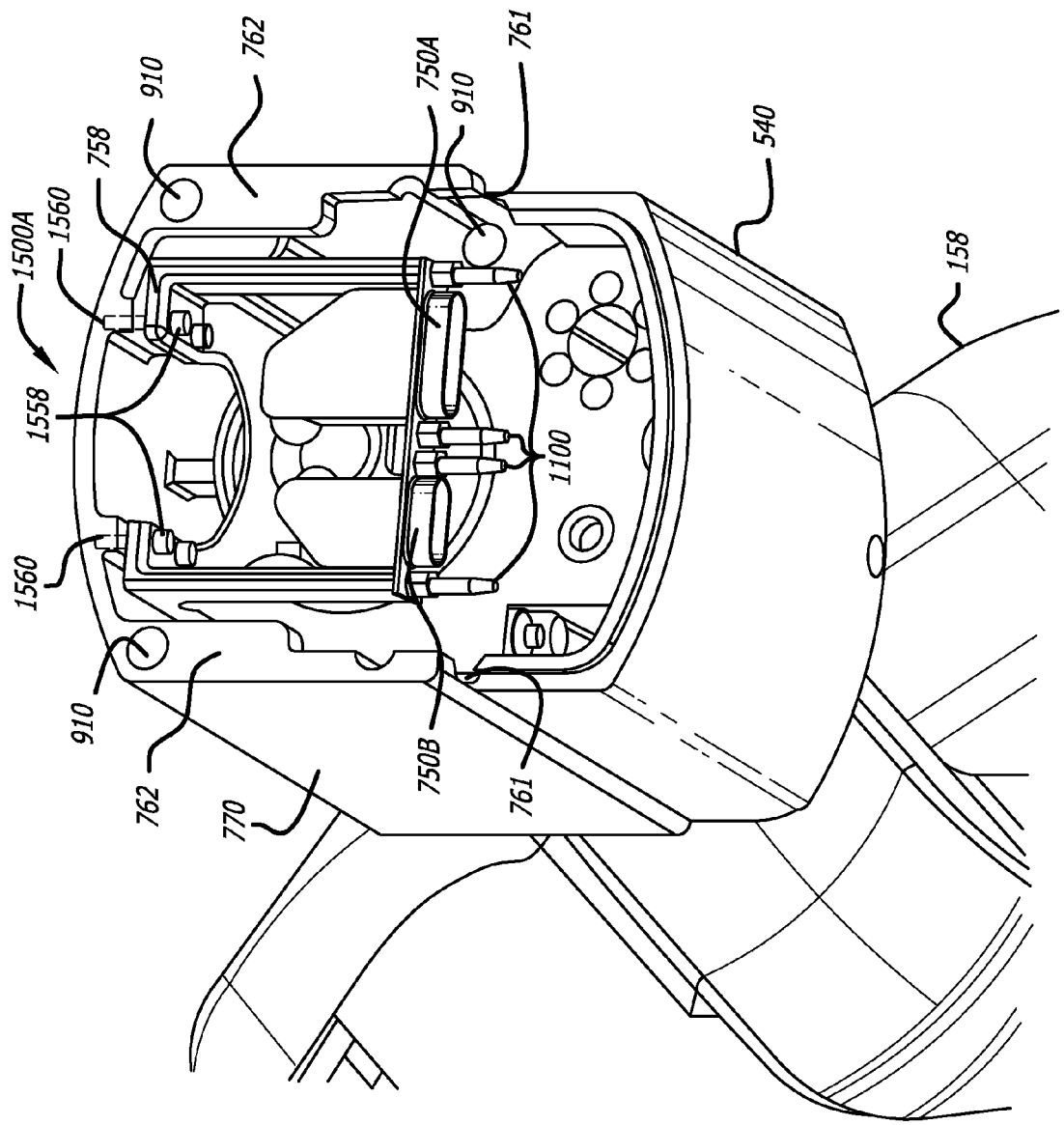
FIG. 15 is an additional perspective view of an exemplary embodiment of the invention.
Figure 16:
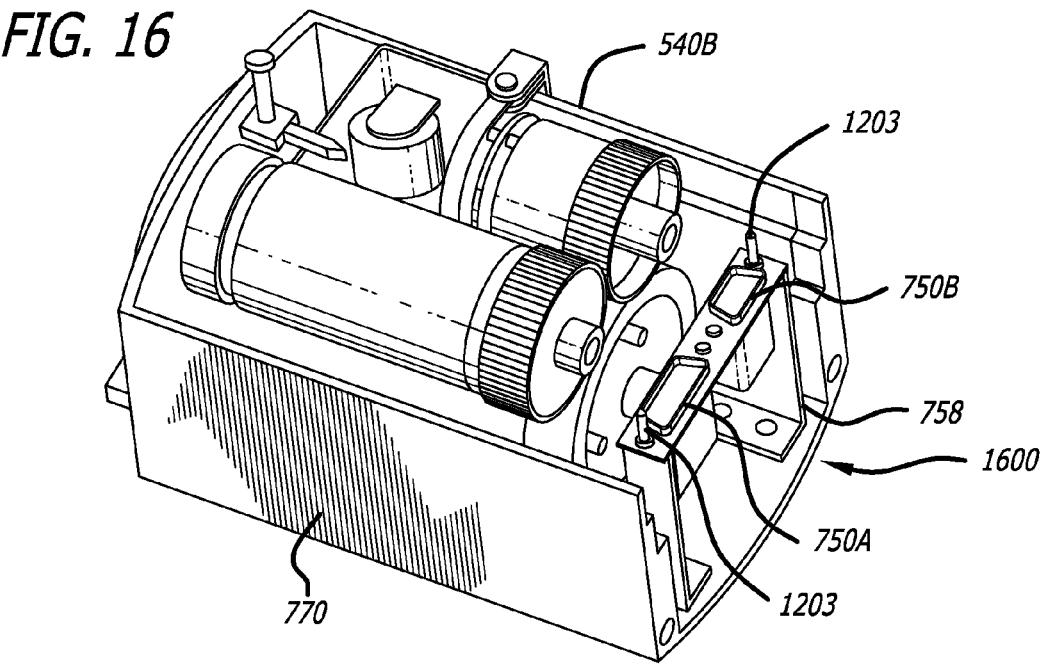
FIG. 16 is a bottom view of an alternate connecting section of the surgical robotic arm to couple to the connector portion of the set up joint portion.

Referring now to FIGS. 15 and 16, connector sections 1500 and 1600 of the SRA portion 540 and 540B are illustrated respectively. The connector sections 1500 and 1600 are substantially similar but for the alignment means used to align the floating electrical connectors 650A and 650B in the connector portion 570 of the SUJ joint 556.

As shown in FIG. 15, the connector section 1500 includes a bracket 758 for supporting a pair of fixed electrical connectors 750A and 750B to be respectively aligned with the flexible or floating electrical connectors 650A and 650B of the connector portion 570 of the SUJ portion 556. The connector section 1500 further includes four guide pins 1100 as shown in FIG. 15 for insertion into four connector holes 1010 of the connector portion 570 to independently align each of the floating electrical connectors 650A and 650B in the set up joint 556.

In contrast, the connector section 1600 includes two outer guide pins 1100 or two alignment pins 1203 shown in FIG. 16 such as to interface to the fifth embodiment of the invention illustrated by FIGS. 13A-13B. The two alignment pins 1203 are inserted into two outer guide holes 1000 and then alignment holes of the mounting bracket 1200 of the connector portion 570 to align both of the floating electrical connectors 650A and 650B together in the set up joint 556. The two inner guide pins 1100 are unnecessary as both floating electrical connectors 650A and 650B move dependently together as part of a common floating bracket 1200.

Each of the connector sections 1500 and 1600 further includes opposing guide slots 761 with flanges 762 for receiving guide tabs 662, and bolt holes 910 for receiving the threaded cylindrical shaft of the bolts 900 but for the heads. The guide tabs 662 of the SUJ portion 556 mates with the flanges 762 of the SRA portions 540, 540B. With the guide tabs 662 fully mated with the flanges 762, the bolts 900 can be used to rigidly couple the SRA portions 540, 540B to SUJ portion 556. The mating of the guide tabs 662 with the flanges 762 reduces the pivoting of the SRA portion 540,540B away from the SUJ portion 556. The bolts 900 inserted through the bolt holes 910 and screwed into the threaded openings 1236 in the SUJ portion, couple the SRA portion 540,540B to the SUJ portion 556 to substantially eliminate any pivoting.

The mounting bracket 758 is coupled to the housing 770 by a plurality of bolts 1558 inserted through openings in the top portion of the bracket and threaded into a plurality of bolt holes 1560. The guide pins 1100 couple to the base of the mounting bracket 758 to point down towards alignment holes in the SUJ portion 556. Also at the base of the mounting bracket 758, the electrical connectors 750A and 750B are held in a fixed position being coupled to the bracket 758 by conventional means. The pins of the electrical connectors 750A-750B point down to mate with the sockets of the electrical connectors 650A-650B which point up.

In one embodiment of the invention, the fixed connectors 750A and 750B of each SRA portion 540,540B are male D-SUB electrical connectors with male pins and the floating electrical connectors 650A and 650B in the connector portion 570 of the setup joint are female D-SUB electrical connector with female pins ("sockets") to receive the male pins and make an electrical connection between each. In an alternate embodiment of the invention, the gender of the connectors is swapped with the fixed connectors 750A and 750B being female D-SUB electrical connectors with female pins ("sockets") and the floating electrical connectors 650A and 650B being male D-SUB electrical connectors with male pins. In one embodiment of the invention, electrical connectors 650A and 750A are 26 pin D-subminiature electrical connectors having a shell size 2 and electrical connectors 650B and 750B are 9 pin D-subminiature electrical connectors having a shell size 1.

Figure 17:
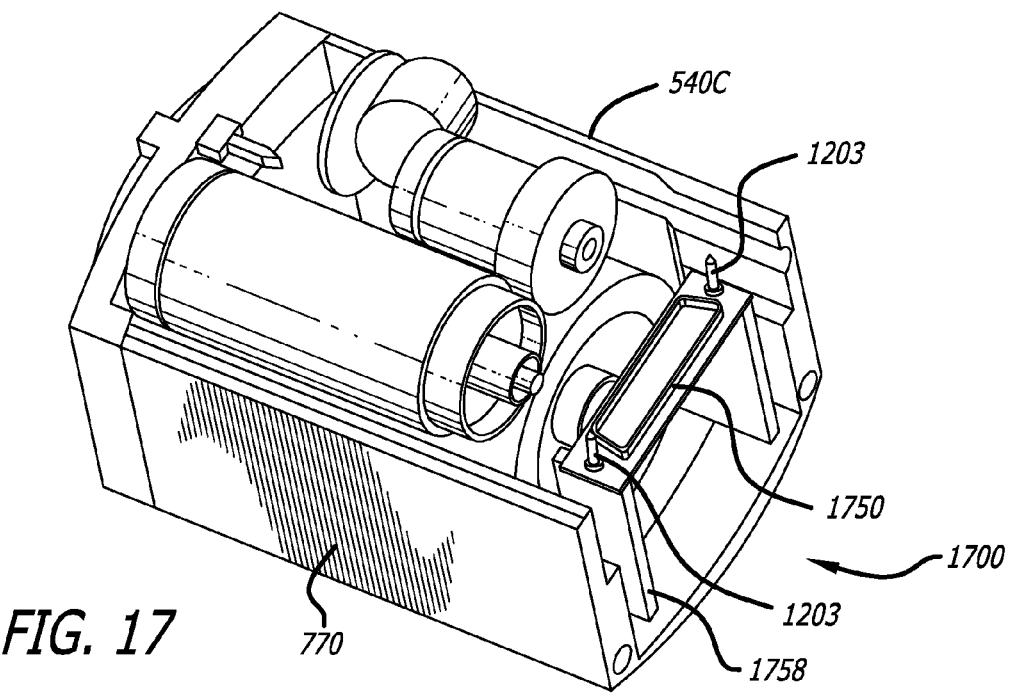
FIG. 17 is a bottom view of an alternate connecting section of the surgical robotic arm to couple to the connector portion of the set up joint portion shown in FIG. 14.

Referring now to FIG. 17, an alternate SRA portion 540C of the robotic surgical arm is illustrated for coupling to the single floating electrical connector 1450 in the connector portion 570 of the setup joint of the third embodiment of the invention illustrated in FIG. 14B. The connector section 1700 of the SRA portion 540C includes two outer alignment pins 1303 and a single fixed connector 1750. The outer alignment pins 1303 are used to move the single floating electrical connector 1450 (see FIG. 14) of the set up joint into alignment to be mated to the single fixed connector 1750 of the SRA portion 540C of the robotic surgical arm.

In one embodiment of the invention, the single fixed connector 1750 of the SRA portion 540C is a male D-SUB electrical connector with male pins and the floating electrical connector 1450 in the connector portion 570 of the setup joint is a female male D-SUB electrical connector with female pins ("sockets") to receive the male pins and make an electrical connection between each. In an alternate embodiment of the invention, the gender of the connectors is swapped with the fixed connector 1750 being a female D-SUB electrical connector with female pins ("sockets") and the floating electrical connector 1450 being a male D-SUB electrical connector with male pins. In one embodiment of the invention, electrical connectors 1450 and 1750 are 43 pin D-subminiature connectors having a shell size 5.

The alternate SRA portion 540C includes a slightly different mounting bracket 1758 over the mounting bracket 758. The base of the mounting bracket 1758 need only hold a single fixed connector 1750 in a fixed position in comparison with the mounting bracket 758. The mounting bracket 1758 may be similarly coupled to the housing 770 by a plurality of bolts 1558 coupled into threaded bolt holes 1560. Alternatively, the mounting bracket 1758 may be molded together and formed as part of the housing 770. Otherwise, the SRA portion 540C of the robotic surgical arm is substantially similar to the SRA portion 540 including its elements described previously.

CONCLUSION

The embodiments of the invention allow for the electrical connections to occur passively as the mechanical connection is made. In order for the electrical connections to occur, one half of each mating electrical connector floats independently of other electrical connectors in one embodiment of the invention. The floating of the electrical connectors reduces misalignment due to the tolerance stack up of the mechanical guide rails and the connectors themselves.

It is advantageous to be able to quickly, reliably and rigidly attach and remove items that have both mechanical and electrical connections. This is especially valuable in surgical manipulators (robotic surgical arms), where time to replace a manipulator should be kept to a minimum. In making both mechanical and the electrical connections together, the embodiments of the invention allow for the electrical connection on one side to float so that it will align correctly to the mating connector under the tight tolerances of the electrical connector without damage due to misalignment from the mechanical connection. Thus, floating the electrical connectors allows multiple connectors to float independently while minimizing the space to do so. Furthermore, only a minimal number of parts are required to constrain any number of electrical connectors and allow them to float independently.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art after reading this disclosure. For example, the floating electrical connectors were described as being part of the connector portion of the set-up joint and set-up arm and the fixed electrical connectors were described as being part of the connector section of the robotic surgical arm. Alternatively, floating electrical connectors may be in the connector section of the robotic surgical arm and the fixed electrical connectors may be a part of the connector portion of the set-up joint and set-up arm. Alternatively, one electrical connector may float in each with the fixed connector in the mating unit. Instead, the embodiments of the invention should be construed according to the claims that follow below.

What is claimed is:

1. A robotic surgical system comprising:
    a set-up arm including
        a first housing;
        a first mounting bracket coupled to the first housing, the first mounting bracket having a left mounting rail with a left guide tab coupled thereto and a right mounting rail with a right guide tab coupled thereto, the first mounting bracket adapted to couple a surgical robotic arm to the set-up arm and support the surgical arm in a suspended position;
        a first electrical connector slidingly coupled to the first mounting bracket to float into alignment; and
        a second electrical connector slidingly coupled to the first mounting bracket to float into alignment.

2. The robotic surgical system of claim 1, wherein
    the first electrical connector and the second electrical connector to float independently of each other and respectively align and mate with a third electrical connector and a fourth electrical connector of the surgical robotic arm.

3. The robotic surgical system of claim 1, wherein
    the first electrical connector and the second electrical connector to commonly float together and respectively align and mate with a third electrical connector and a fourth electrical connector of the surgical robotic arm.

4. The robotic surgical system of claim 1, wherein
    the first housing, the first mounting bracket and the first electrical connector and the second electrical connector are part of a set-up joint of the set-up arm.

5. The robotic surgical system of claim 1, wherein the surgical robotic arm comprises:
    a second housing having a left guide slot with a left flange and a right guide with a right flange;
    a second mounting bracket coupled to the second housing, the second mounting bracket;
    a third electrical connector rigidly coupled to the second mounting bracket;
    a fourth electrical connector rigidly coupled to the second mounting bracket; and
    a plurality of guide pins coupled to the second mounting bracket, the plurality of guide pins to align the first electrical connector to mate with the third electrical connector and to align the second electrical connector to mate with the fourth electrical connector.

6. The robotic surgical system of claim 5, wherein
    the left guide slot and the right guide slot of the second housing to respectively slide along the left mounting rail and the right mounting rail of the first mounting bracket to mate the left flange of the second housing with the left guide tab of the first mounting bracket and the right flange of the second housing with the right guide tab of the first mounting bracket to reduce pivoting of the robotic surgical arm out from the set-up arm.

7. The robotic surgical system of claim 5, further comprising:
    a plurality of bolts each having a head coupled to the second housing and a threaded shank inserted into openings in the second housing and screwed into threaded bolt holes of the first housing to rigidly couple the robotic surgical arm to the set-up arm.

8. The robotic surgical system of claim 5, wherein
    the first electrical connector and the second electrical connector float independently of each other, and
    the plurality of guide pins includes a first pair of guide pins to align the first electrical connector to mate with the third electrical connector and a second pair of guide pins to align the second electrical connector to mate with the fourth electrical connector.

9. The robotic surgical system of claim 5, wherein
    the first electrical connector and the second electrical connector commonly float together, and
    the plurality of guide pins includes at least one pair of guide pins to commonly align the first electrical connector and the second electrical connector together to respectively mate with the third electrical connector and the fourth electrical connector.

* * * * *